(12) United States Patent
Relin

(10) Patent No.: US 8,177,825 B2
(45) Date of Patent: May 15, 2012

(54) METHOD OF DYNAMIC BINARY TEMPERATURE THERAPY

(75) Inventor: Arkadi Relin, Langhorne, PA (US)

(73) Assignee: REMCO International, Inc.

( * ) Notice: Subject to any disclaimer, the term of this patent is extended or adjusted under 35 U.S.C. 154(b) by 681 days.

(21) Appl. No.: 12/315,948

(22) Filed: Dec. 9, 2008

(65) Prior Publication Data
US 2009/0149928 A1 Jun. 11, 2009

Related U.S. Application Data

(60) Provisional application No. 61/005,931, filed on Dec. 10, 2007.

(51) Int. Cl.
*A61F 7/00* (2006.01)
*A61F 7/12* (2006.01)
(52) U.S. Cl. .......................................... 607/96; 607/108
(58) Field of Classification Search .............. 607/96–99, 607/103, 104, 108–112, 114
See application file for complete search history.

(56) References Cited

U.S. PATENT DOCUMENTS

| | | | |
|---|---|---|---|
| 2002/0156509 A1* | 10/2002 | Cheung | 607/96 |
| 2009/0012436 A1* | 1/2009 | Lanfermann et al. | 602/2 |

* cited by examiner

*Primary Examiner* — Matthew F DeSanto

(57) ABSTRACT

In a dynamic contrast temperature system including a thermocycling block and an organism zone multi-modules temperature applicator a method of spatiotemporal temperature-physiological optimizing includes modules structure arranging and modulating a module temperature action with a law, a range and a frequency providing a cooling phase and a heating phase of a "drop-shaped" form law so, that each two side by side disposed the modules form a temperature pair with a modulated binary temperature action gradient, and a modulation comparative phase provides a phase shift to a comparative phase of an independent periodic additional action process; and gradient-wave therapeutically optimized changing the modulation parameters in dependence on the changes of the organism physiological characteristics.

43 Claims, 7 Drawing Sheets

METHOD OF DYNAMIC BINARY TEMPERATURE THERAPY

TECHNICAL FIELD

The present invention relates to the methods, which provide a temperature action on the selected application organism zone. It encompasses a broad class of various devices and systems, which are using for the different temperature therapeutical, relaxation, massage and cosmetic procedures, etc.

BACKGROUND ART

In the present time, the various methods, devices and systems are known, which provide a temperature action on the selected application organism zone. A common traditional methodological approach, which is used in the above-mentioned various methods, devices (or systems), is the application of an integrally constant in time temperature (cold or warm) action on all selected application organism zone during the procedure process. Such devices (or systems) using the various known types and forms of hard or elastic temperature applicators, which provide the above-mentioned temperature (cold or warm) action on all selected application organism zone during the procedure process.

Herewith, the traditional thermo-accumulation temperature applicators can be previously cooled (or warmed) by the additional temperature means, which is constant not connected with the applicator (for example: a cooler, a heater, cold or warm water, etc). The elastic such temperature applicators, for example the different so-called "Hot/cold gel face masks" or "Thermassage neck wraps", can be filled with non-toxic gel for the accumulation of cold (or warm), and also—can be filled with cooling absorbed crystals (for example, in the different so-called "Head bands"). Besides, the traditional hard thermo-generation temperature applicators can includes the temperature means, which is constant constructive connected with the applicator (for example: a cooler or a heater element). The examples of such (around neck) temperature applicators can be the different so-called "Personal warm or cold systems", with a miniaturized heat pump based on the so-called Peltier Effect—a thermoelectric principle whereby one direction of an electric current allows heat to be absorbed on one side of the aluminum neck plate (making it cold) as heat is rejected on the other (making it warm). The constant change of electron flow direction in said heat pump, and also—the constant "cold" or "warm" regimes realizing in such systems by the hand switch.

Common disadvantages of the similar known traditional methodological approach, which is realized in such devices (or systems) for providing of the integrally constant in time temperature action process, are as follows:
 the limited temporal possibilities, which physiological embargo (in majority of the above-mentioned applications) for continual integrally constant in time temperature (cold or warm) action on all selected application organism zone during the temperature action process;
 the limited possibilities for local selectivity of temperature (cold or warm) action on selected application organism zone during the temperature action process;
 the limited possibilities for a temperature-physiological optimization of the temperature action process.

The above-listed basic disadvantages significantly reduce temperature-physiological efficiency of application of such traditional devices (or systems), which provide the integrally constant in time temperature (cold or warm) action on all selected application organism zone during the procedure process.

Other methods and devices (or systems), which realize the methodological approach is used the integrally periodical dynamic variable in time temperature (cold-warm) action on all selected application organism zone during the procedure process are known, as disclosed for example in U.S. Pat. No. 5,358,467 (1994)—A. Relin, et al. (creation in Remco International, Inc., PA, USA). In the above-mentioned example the dynamic temperature (cold-warm) action on said organism zone periodic realizing of a fluid matter (air flow), which previously periodical cooled and warmed by the additional temperature means included in the massage device. At that, said massage device provides also a periodical dynamic in-phase vacuum and mechanical actions on said organism zone, simultaneously with said periodical dynamic temperature (cold-warm) action.

The above-mentioned realization of said periodical dynamic temperature (cold-warm) action on selected organism zone predetermine a significantly increase of a physiological efficiency of such integrally periodical temperature (air flow) action. Herewith, the above-mentioned significantly disadvantage: the limited temporal possibilities, which physiological embargo (in majority of the above-mentioned applications) for continual integrally constant in time temperature (cold or warm) action on all selected application organism zone during the temperature action process, practically eliminate.

At the same time, such integrally periodical dynamic temperature (cold-warm) action methodological approach also describes of the above-mentioned basic significantly disadvantages, reducing a temperature-physiological efficiency of its application:
 the limited possibilities for local selectivity of temperature (cold-warm) action on selected application organism zone during the temperature action process; and
 the limited possibilities for a dynamic local spatiotemporal temperature-physiological optimization of the dynamic temperature action process.

The above-mentioned basic significantly disadvantage: the limited possibilities for local selectivity of temperature (cold-warm) action on selected application organism zone during the temperature action process, practically eliminate in other known method of and device for local skin massage (cosmetic purpose), as disclosed for example in U.S. Pat. No. 5,746,702 (1998)—"Assignee" is A. Relin (Remco International, Inc., PA, USA). Elimination of said disadvantage providing by the methodological approach is used the fixed in time synchronous local periodical dynamic variable temperature (cold-warm) actions on selected application organism local zones during the procedure process.

Said methodological approach realizing by several temperature local applicators (so-called "massage thermoelectric blocks") with thermal elements operating on the base of so-called Peltier Effect and is electric connected with a block of automatic contrast thermocycling by electric network. In said patents the device for local skin massage includes two such local temperature applicators for synchronous local periodical dynamic variable in time temperature (cold-warm) actions on two selected temple areas of a patient's head as the local skin portions for the temperature stimulation, accordingly. The block of automatic contrast thermocycling providing the automatic performance of fixed given temperature-time cycle, including carrying out of synchronous sign-alternating processes of change of electric currents flowing through the thermal elements of said two in series connected massage thermoelectric blocks simultaneously. Herewith, a constant value of infra-low frequency (at least $5\cdot10^{-3}$ Hz) of said electric currents impulse change, and also a fixed constant values and time of sign-alternating electric currents impulses by the block of automatic contrast thermocycling fixed synchronous providing. The above-mentioned automatic process provides a fixed predetermined contrast change of temperatures of impulse cooling and impulse heating said two massage thermoelectric blocks on said two fixed diversity selected temple areas of a patient's head simultaneously (for example, not exceeding ±25° C. relative to an initial temperature of a corresponding one of the local skin portions). Herewith, the general vector of temperature gradient (cold-warm) action is normal to the temperature applicator contact surface.

The above-mentioned fixed synchronous local periodical dynamic temperature (cold-warm) actions methodological approach significantly increase of a local physiological efficiency and extend the possibilities of use of such local periodical dynamic temperature (cold-warm) actions at the decision of the different temperature therapeutical, relaxation, massage and cosmetic procedure problems.

At the same time, such dynamic methodological approach demands a creation of fundamentally new possibilities for a dynamic local spatiotemporal temperature-physiological optimization of the dynamic temperature action process, which will eliminate all local orientated dynamic temperature (cold-warm) actions optimization limitations of the above-mentioned approach.

SUMMARY OF THE INVENTION

Accordingly, it is an object of the present invention to provide a new method of dynamic binary temperature therapy, which is based on new modulation and optimization multipoint wave temperature (cold-warm) actions principles.

The proposed method is based on the results of multi-years scientific researches of Dr. A Relin, developing of the concept of new theory "Dynamic differential-residual (binary) temperature action on the structure of object." Said scientific researches posited the goals, connected with the solutions of series of the basis principle new scientific-practical problems:

the establishment of scientifically-founded laws of said modulating a value of temperature (cold-warm) action on selected application organism local zone during the procedure process, providing the most local temperature-physiological efficiency of dynamic binary temperature therapy process and one correlation connecting the others general predetermined modulation parameters (a frequency and a range);

the establishment of scientifically-founded range for a choice of a frequency of said modulating the temperature (cold-warm) actions, providing the most spatiotemporal temperature-physiological efficiency of dynamic binary temperature therapy actions wave process;

the establishment of the scientifically-founded criterions of the spatiotemporal temperature-physiological optimization of said multi-point wave temperature (cold-warm) actions to realize said new method of dynamic binary temperature therapy;

the establishment of the scientifically-founded new additional time parameter of said temperature modulating, providing the most of spatiotemporal temperature-physiological efficiency of dynamic binary (differential-residual) temperature therapy actions wave process;

the establishment of the scientifically-founded new additional time parameter of said temperature modulating, providing the most of spatiotemporal temperature-physiological efficiency of dynamic binary (differential-residual) temperature therapy actions wave process, when said modulated temperature therapy actions related with at least one an additional independent process of predetermined periodic action on said object;

the establishment of the scientifically-founded spatial temperature therapy action zone structures to realize the dynamic spatiotemporal temperature-physiological efficient wave process of the binary temperature therapy actions.

For the first time these scientific researches allowed to propose the new most spatiotemporal temperature-physiological effective modulation and optimization principles of said multi-point wave contrast temperature (cold-warm) actions for realizing said method. Herewith, the general problem was to provide the maximal effective of dynamic optimizing spatiotemporal differential-residual (binary) temperature-physiological interaction between said multi-point wave contrast temperature (cold-warm) actions and the hemodynamic wave physiological processes of blood circulation in the capillaries, arteries and veins of the selected application organism zone.

At the first time proposed multi-vector wave spatiotemporal differential-residual contrast temperature (cold-warm) actions takes into consideration the general role of brachiate capillary structures and wave processes between capillaries in said physiological processes of tissue blood circulation. In the all capillaries of organism simultaneously stand by until eighty percentages of the circulation blood. Besides, the quality of functioning of brachiate capillary structure touch on the vascular and tissue physiological systems. Herewith also take into consideration, that genesis of the different pathologies in said capillaries—pulsating organs (congestion, mutation of wall or diameter, and also—spasm of capillaries, or availability into capillaries of harmful substances, etc.) predetermine the significant failure of peripheral capillary tissue blood circulation, and well then—the physiological affection in said application organism zone. Besides, said physiological affection can be predetermined also and such said different pathologies in said vascular physiological system (congestion, mutation of wall or diameter, and also—spasm of vascular, or availability into vascular of harmful substances, etc.).

At the same time the researches proved, that said blood circulation systems and tissue nervous ends of most different organism zones physiological actively interact with the different algesis temperature-sensitive receptors, reactive only on the specific dynamic temperature (cold-warm) diapason and blocking the nerve transfer of a painful information. Herewith, the analgesics receptors potential there is on the both ends of said dynamic temperature (cold-warm) diapason.

At the same time, by the author is researched and proved one's case of the great efficiency of use of said dynamic differential-residual contrast temperature (cold-warm) actions for the minimization or radical elimination of the above-mentioned physiological affection in said application organism zone. Said efficiency providing the realization of physiological effective dynamic differential-residual contrast temperature (cold-warm) so-called "massage" and "wave smoothing" of blood circulation zone capillary/vascular system (or so-called "temperature-dynamic physiological correction"). Thus the proposed binary temperature (cold-warm) therapy actions is ordered on the treatment of said functional defections in said organism zone capillary and vascular structures, which significant influence on the vital physiological processes in zone tissues (so-called "binary temperature capillary/vascular therapy").

In keeping with these objects and with others, which will become apparent hereinafter, one of the new features of the present invention resides, briefly stated, in a new method of dynamic binary temperature therapy, which includes the following.

In a dynamic binary (differential-residual) temperature therapy system for providing a dynamic multi-point wave contrast temperature (cold-warm) action on the selected application organism zone in a physiological process of the different temperature therapeutical, relaxation, massage and cosmetic procedures, including at least one a block of automatic contrast thermocycling, which is connected with at least one a multipoint temperature applicator with a plurality dynamic temperature modules, including at least one a thermal element, contacting with said zone and providing a dynamic temperature actions on a plurality selected local portions of said organism zone during the procedure process accordingly; a method of spatiotemporal temperature-physiological optimization, comprising the steps of:

arranging each of said plurality dynamic temperature modules above each of said plurality local organism zone surface portions selected and disposed at said zone surface per at least one given type temperature action surface structure so that each two side by side disposed of said working dynamic temperature modules form a dynamic "spatial" differential-residual temperature pair on said zone surface, which is externally limited by an external borders of said two selected local zone portions accordingly;

general modulating a value of said temperature action of at least one said dynamic temperature module of at least one said "spatial" dynamic temperature pair accordingly so that said working temperature pair forming a modulated gradient of a differential-residual spatial temperature action (between said temperature modules) in an organism zone portion, which is externally limited by an external borders of two said selected local zone surface portions contacting with said dynamic temperature modules of said "spatial" dynamic temperature pair, accordingly;

said general modulating includes providing a frequency, a range and a law as a general predetermined modulation parameters;

said modulating includes providing a comparative phase as an additional predetermined modulation parameter, when said modulated temperature action related with at least one an independent predetermined periodic process, which realizing simultaneously with said modulating and provides an additional action on said organism;

said period of general modulating includes providing a cooling phase and a heating phase, and also—an additional predetermined resting phase, which can be used after a termination of said cooling or/and heating phases; and also changing a value of at least one said modulation parameter in dependence on a change of a value of at least one a characteristic connected with the physiological processes of said organism for providing a maximal therapeutically effective optimizing of said modulated temperature action, in the binary temperature gradient-wave manner, during said process.

The above-mentioned given binary temperature action surface structure of a disposition of said working dynamic temperature modules, forms a dynamic "spatial" differential-residual temperature pairs on said organism zone surface, can be a different types, without any limitation, for example:

the longitudinal linear binary temperature action surface structure;

the longitudinal nonlinear(for example: sinusoidal, triangular, rectangular, trapezoidal, voluntary form, etc.) binary temperature action surface structure;

the circular binary temperature action surface structure;

the coaxial-circular binary temperature action surface structure;

the radially-circular binary temperature action surface structure;

the geometrical figure (sinusoidal, triangular, rectangular, trapezoidal, elliptical, etc.) binary temperature action surface structure; and etc.

At that the above-mentioned different types of said binary temperature action surface structure can be formed with use, for example:

a serial disposition of separate along formative line at least two said formed dynamic "spatial" differential-residual temperature pairs, each from which serial creation an unidirectional or/and antidirectional modulated gradient of a differential-residual (binary) "spatial" temperature actionin a zone portion accordingly; or a serial disposition of so-called "related" along formative line at least two formed said dynamic "spatial" differential-residual temperature pairs with one joint said dynamic temperature module, which is collected for each twoserial disposed said dynamic temperature pairs, each from which serial creation an antidirectional modulated gradient of a differential-residual (binary) "spatial" temperature action in a zone portion accordingly.

The above-mentioned multi-point temperature applicator with a plurality dynamic temperature modules can comprise as one of such given binary temperature action surface structure, so and at least two of such structures, which are disposed together relatively each other on an application binary temperature action surface of said applicator, without any limitation, for example:

in series along formative line;

parallel (with symmetrical or nonsymmetrical disposition of said dynamic "spatial" differential-residual temperature pairs in said parallel structures);

in series—parallel along formative line;

perpendicular;

under given angle; etc.

Herewith, a disposition of at least one said dynamic temperature module in a construction of said binary temperature action applicator can be as fixed, so and adjustable for the possibility of correction of a disposition as at least one said dynamic "spatial" differential-residual (binary) temperature pair, so and all given form of said binary temperature action surface structure accordingly.

At the same time, a form of a contact temperature action surface of said dynamic temperature modules of such the above-mentioned multi-point temperature applicator can be the same or different (without any limitation, for example: flat, oval, multi-faceted and etc.). Herewith, such binary temperature action applicator can have the different forms and as a superposed on said different forms organism zone surfaces, so and a catheterized in a different forms internal cavities of said organism. At the same time, said such binary temperature action applicators can be a constructively removed with the different elements for fixing on said application organism zone surfaces of different forms, without any limitation, for example:

the different types of elastic adhesives or zipped so-called "binary temperature (cold-warm) action frontal-head bands";

the different types of elastic adhesives or zipped so-called "binary temperature (cold-warm) action temporal-head bands";

the different types of elastic adhesives or zipped so-called "binary temperature (cold-warm) action eye bands";

the different types of elastic spring, adhesives or zipped so-called "binary temperature (cold-warm) action head slams";

the different types of elastic spring, adhesives or zipped so-called "binary temperature (cold-warm) action neck wraps";

the different types of elastic spring, adhesives or zipped so-called "binary temperature (cold-warm) action face masks";

the different types of spring so-called "binary temperature (cold-warm) action nose clips";

the different types of spring so-called "binary temperature (cold-warm) action auricular clips";

the different types of spring so-called "binary temperature (cold-warm) action general at least two-point clips";

the different types of elastic adhesives or zipped so-called "binary temperature (cold-warm) action bandages";

the different types of elastic adhesives or zipped local so-called "binary temperature (cold-warm) action sticking-plasters";

the different types of elastic spring, adhesives or zipped so-called "binary temperature (cold-warm) action bracelets";

the different types of elastic spring, adhesives or zipped so-called "binary temperature (cold-warm) action shoulder cups";

the different types of elastic spring, adhesives or zipped so-called "binary temperature (cold-warm) action ancoenal cups";

the different types of elastic spring, adhesives or zipped so-called "binary temperature (cold-warm) action genicular cups";

the different types of elastic spring, adhesives or zipped so-called "binary temperature (cold-warm) action amputating cups";

the different types of elastic spring, adhesives or zipped so-called "binary temperature (cold-warm) action spine stimulating tapes";

the different types of elastic spring, adhesives or zipped so-called "binary temperature (cold-warm) action gloves";

the different types of elastic spring, adhesives or zipped so-called "binary temperature (cold-warm) action socks";

the different types of so-called "binary temperature (cold-warm) action hand stimulating baths";

the different types of so-called "binary temperature (cold-warm) action foot stimulating baths";

the different types of elastic (spring or inflatable) so-called "binary temperature (cold-warm) action internal stimulating applicators"; and etc.

At that said multi-modules temperature internal stimulating applicator can be a bulk device with an outside elastic form of multi-modules contact temperature action surface, profile optimizing by said application organism zone internal surface under at least one an applicator mechanical action, which is selected from the group, without any limitation, consisting of: an action of elastic deformation of said elastic applicator bulk device; an action of elastic element on interior surface of hollow elastic applicator bulk device; an action of fluid medium pressured on interior surface of hollow inflatable elastic applicator bulk device; and etc.

Besides, such binary temperature action applicators (for example, flexible network applicators) can be constructively or/and functional connected with at least one an other functional system, and also—a constructively built-in into a structure of a various different wares with a surface, which can be continually contacted with said application organism zone surfaces of different forms, without any limitation, for example:

the fabric for different close-fitting clothes, linen, gloves, headdress, bed components, shoes components;

the different surfaces of furniture components, for example: armchair, divan, table;

the different functional components of various functional systems, for example: rudder of car; mouse or keyboard elements of computer; elements of glasses, headphones, wrist-watch, telephone, musical device, medical equipment; and etc.

Another important feature of the present invention is that the above-mentioned said predetermined law of said general modulating a value of said temperature action of at least one said dynamic temperature module of each said "spatial" dynamic temperature pair can be different types for providing said dynamic spatiotemporal temperature-physiological optimize of said physiological process, without any limitation, for example: sinusoidal, triangular, rectangular, trapezoidal, elliptical, etc. Herewith, said predetermined modulation law comprises a predetermined cooling phase law and a predetermined heating phase law, which can be the same or different forms. Herewith, phase duration and maximal temperature (cold or warm) action phase amplitude of said predetermined cooling phase and predetermined heating phase can be also the same or different, accordingly. Said additional predetermined resting phase can have a different resting duration, including zero. At the same time, maximal value of said predetermined modulation frequency, which predetermines a minimal period of said general modulating is changed so that provide given value of the dynamic differential-residual temperature field action at given temperature (cold-warm) range and a law action change.

The important feature of the present invention is that the above-mentioned predetermined cooling phase law and/or predetermined heating phase law is the "drop-shaped" form selected, which is named by Dr. A. Relin—"drop-shaped form cooling/heating phase law". Said "drop-shaped cooling/heating phase law" includes providing increase of a value of said temperature (cold or warm) action from the initial null value (when selected local zone portion of organism surface, contacting with said dynamic temperature module, have a current value of natural temperature) on a predetermined maximal temperature (cold or warm) action phase amplitude during a predetermined front time of realizing a predetermined front short part of said "drop-shaped" form of said phase law, and providing decrease of a value of said temperature (cold or warm) action until the initial null value (providing recovery of a current value of natural temperature of a selected local zone portion of organism surface, contacting with said dynamic temperature module) during a predetermined back time of realizing a predetermined back extended part said "drop-shaped" form of said phase law during a predetermined duration of cooling (or heating) phase in an each period of said temperature (cold-warm) action modulating is changed to provide a predetermined modulation frequency.

At the same time the predetermined front short part of "drop-shaped" form of said so-called "drop-shaped cooling/heating phase law" is changed a form of a predetermined quarter ellipse curve such that a horizontal axis of said ellipse coincides with a horizontal axis of said "drop-shaped" form of said phase law, and said predetermined back extended part of "drop-shaped" form of said phase law is changed a form of a predetermined degree function curve such that an initial value of said degree function curve coincides with an ending value of said quarter ellipse curve.

The above-mentioned predetermined "drop-shaped" form of said phase law includes providing a predetermined value of time ratio of said predetermined front time into said predetermined phase duration of cooling (or heating) phase, and a value of said predetermined time ratio is selected from the range: more than 0 and less than 0.5. The value of time ratio is more one of an additional predetermined modulation parameter of said temperature modulating and can be changeable in dependence on a change of a value of at least one a characteristic connected with the physiological processes of said organism for providing an optimizing maximal efficiency of said modulated differential-residual spatial temperature action during said physiological procedure process. Herewith, a predetermined value of time ratio of said cooling and heating phases in an each period of said temperature (cold-warm) action modulating can be also the different or same, accordingly.

Said changes of said value of time ratio can include:
changing a predetermined front time and providing a predetermined duration of cooling (or heating) phase simultaneously;
changing a predetermined duration of cooling (or heating) phase and providing a predetermined front time simultaneously;
changing a predetermined front time and a predetermined duration of cooling (or heating) phase simultaneously.

In accordance with another feature of the present invention, said temperature (cold-warm) action modulating includes providing a predetermined comparative phase, which is optimization changed to provide a phase shift to a comparative phase of said independent predetermined periodic process, which affects to said organism simultaneously with said temperature general modulating. At the same time the independent predetermined periodic process includes providing a frequency, a range, a law and a comparative phase of a predetermined periodic parametric changes.

The above-mentioned independent predetermined periodic process can include, without any limitation, for example:
providing an additional independent predetermined modulating a value of said temperature action of said second dynamic temperature module of at least one said "spatial" dynamic temperature pair accordingly so that said working temperature pair creation a modulated-residual gradient of a differential-residual temperature field action between said two dynamic working temperature modules in said local zone surface area, which is externally limited by an external borders of said two selected local zone portions contacting with said dynamic temperature modules of each said "spatial" dynamic temperature pair, accordingly;
providing an additional independent predetermined modulating a value of said temperature action of at least one a dynamic temperature module of at least one said "spatial" dynamic temperature pair accordingly, which is disposed in at least one the above-mentioned other binary temperature action surface structure of the same multi-point temperature applicator with a plurality dynamic temperature modules;
providing an additional independent predetermined modulating a value of said temperature action of at least one a dynamic temperature module of at least one said "spatial" dynamic temperature pair accordingly, which is disposed in at least one the above-mentioned other binary temperature action surface structure of an other multi-point temperature applicator with a plurality dynamic temperature modules for a dynamic temperature action on other said organism zone;
providing an independent predetermined periodic change of a value of at least one an additional other type action on an organism zone (same or other), an organism organ or on all said organism, without any limitation, for example: a mechanical, a vacuum, other type temperature, a light (or color), a visual, a musical (or sound), an energy field, or a fluid medium (gas, fluidic or dosing for delivery of a medicamental preparation) action; and etc.

Herewith, the above-mentioned additional independent predetermined modulations can comprising the same or different forms of a predetermined cooling phase law and a predetermined heating phase law as by realization of said independent modulations, so and relatively of the above-mentioned general modulation. A duration and maximal temperature (cold or warm) action amplitude of said predetermined cooling phase and predetermined heating phase of said additional independent predetermined modulations can be also the same or different, accordingly. At that, after a termination of at least one from said cooling phase and a heating phase can be provided an additional resting phase with predetermined resting duration (including zero), when a value of said temperature action is equal to null.

In accordance with another feature of the present invention, the above-mentioned general and additional predetermined modulations comprise a modulation parametric input and an optimization parametric input.

The above-mentioned characteristics, which is connected with a physiological processes of said organism can be selected from the group, without any limitation, for example consisting of: a blood pressure; a vascular or capillary blood velocity; a central, coupled, collapsing, identification, full or bounding pulse; a local capillary pulsation; a local or integral temperature; a space organism zone temperature allocation; etc.

The important feature of the present invention is that the above-mentioned each dynamic temperature (cold-warm) module includes at least one a thermal element operating on the base of so-called Peltier Effect, which is electric connected with a block of automatic contrast thermocycling by electric network. Herewith providing a possibility of predetermined change of cooling and heating temperatures of said dynamic temperature module action on said local portions of said organism zone accordingly by the automatic performance of given carrying out sign-alternating process of optimizing modulation change of electric current, flowing through the thermal elements of said dynamic temperature (cold-warm) module. At that said dynamic temperature modules, which electric connected with said block, can be electric connected together per the different groups (in series, parallel or mix), and also can be electric no connected together at given organization of the above-mentioned different types of binary temperature action surface structure, using said dynamic "spatial" differential-residual temperature pairs.

At the same time, the above-mentioned each dynamic temperature module can include at least one a thermal element operating on the base at least one a different effect realizing of temperature (cold or/and warm) action, which is selected from the group, without any limitation, for example consisting of: electro-thermal, electro-magnetic, electro-chemical, electro-optical or laser, etc.

In accordance with another feature of the present invention, the above-mentioned at least one dynamic temperature module of the above-mentioned different types of binary temperature (cold-warm) action surface structure, using said dynamic "spatial" differential-residual temperature pairs, can be functional consisted with at least one an additional different functional device (or element), without any limitation, for example:

- the dosing device for delivery of a medicamental preparation or salve on a local portion of said organism zone surface, which is contacted with said temperature module;
- the mechanical one-point or multi-point device for mechanical action on a local portion of said organism zone surface, which is contacted with said temperature module;
- the vacuum one-point or multi-point device for vacuum action on a local portion of said organism zone surface, which is contacted with said temperature module;
- the one-point or multi-point indicator light element for generation dynamic wave light (color) picture correlating with dynamic change of temperature (cold-warm) action amplitude, which can be disposed, for example: on the exterior surface of said temperature module or the above-mentioned binary temperature action applicator, and also—on the special functional light indicator panel for a dynamic light (color) visualization of spatiotemporal picture of binary temperature (cold-warm) multi-point action on said organism zone surface, which is disposed under said applicator;
- the one-point or multi-point indicator sound element for generation dynamic wave sound image, correlating with dynamic change of temperature (cold-warm) action amplitude;
- the one-point or multi-point sensor for a control of one from the above-mentioned characteristics, which is connected with a physiological processes of said organism selected from the group, without any limitation, for example consisting of: a blood pressure; a vascular (capillary) blood velocity; a central, coupled, collapsing, identification, full or bounding pulse; a local or integral temperature; space temperature allocation; etc.

At least one of such sensor and also additional different functional device or element for action (for example: dosing, mechanical or vacuum) on local portions of said organism zone surface can be disposed between said dynamic temperature modules and functional consisted with the interior surface of the above-mentioned binary temperature action applicator. Said additional functional elements or devices, and also—said sensors or/and indicator elements (light or sound) can be electric connected with said block of automatic contrast thermocycling by electric network.

At the same time, said such additional different functional element or device for action can provide the above-mentioned independent predetermined periodic process of change (or modulation) of a value of said additional action (for example: dosing, mechanical or vacuum) on said organism zone surface, which is characterized a predetermined comparative phase. Herewith, it will be provided the above-mentioned optimization changeable phase shift between a comparative phase of said independent predetermined periodic process and a predetermined comparative phase of said temperature (cold-warm) action modulating.

The above-mentioned method of spatiotemporal temperature-physiological optimization provides the possibility of effective use of the present method of dynamic binary temperature therapy in said physiological processes, which are connected with one from the different type application groups of known temperature therapeutical, relaxation, massage and cosmetic procedures, without any limitation, for example:

- the treatment of headache;
- the treatment of migraine;
- the treatment of coronary insufficiency;
- the treatment of neuropathical pain;
- the treatment of functional spasm process;
- the treatment of hemostasis process;
- the treatment of haematomas process;
- the treatment of swelling process;
- the treatment of zone fracture;
- the treatment of zone surgical seam;
- the treatment of blood circulation violation in amputated zone;
- the treatment of painful autosomatognosis;
- the treatment of painful arthritis;
- the treatment of locomotor apparatus violation;
- the treatment of hair radical system violation;
- the treatment of cosmetic violation;
- the general brain-fag; and etc.

The novel features which are considered as characteristic for the present invention are set forth in particular in the appended claims. The invention itself, however, both as to its construction and new method of operation, together with additional objects and advantages thereof, will be best understood from the following description of specific embodiments when read in connection with the accompanying drawings.

DESCRIPTION OF THE PREFERRED EMBODIMENTS

A proposed new method of dynamic binary temperature therapy can be realized in the following manner.

Figure 1:
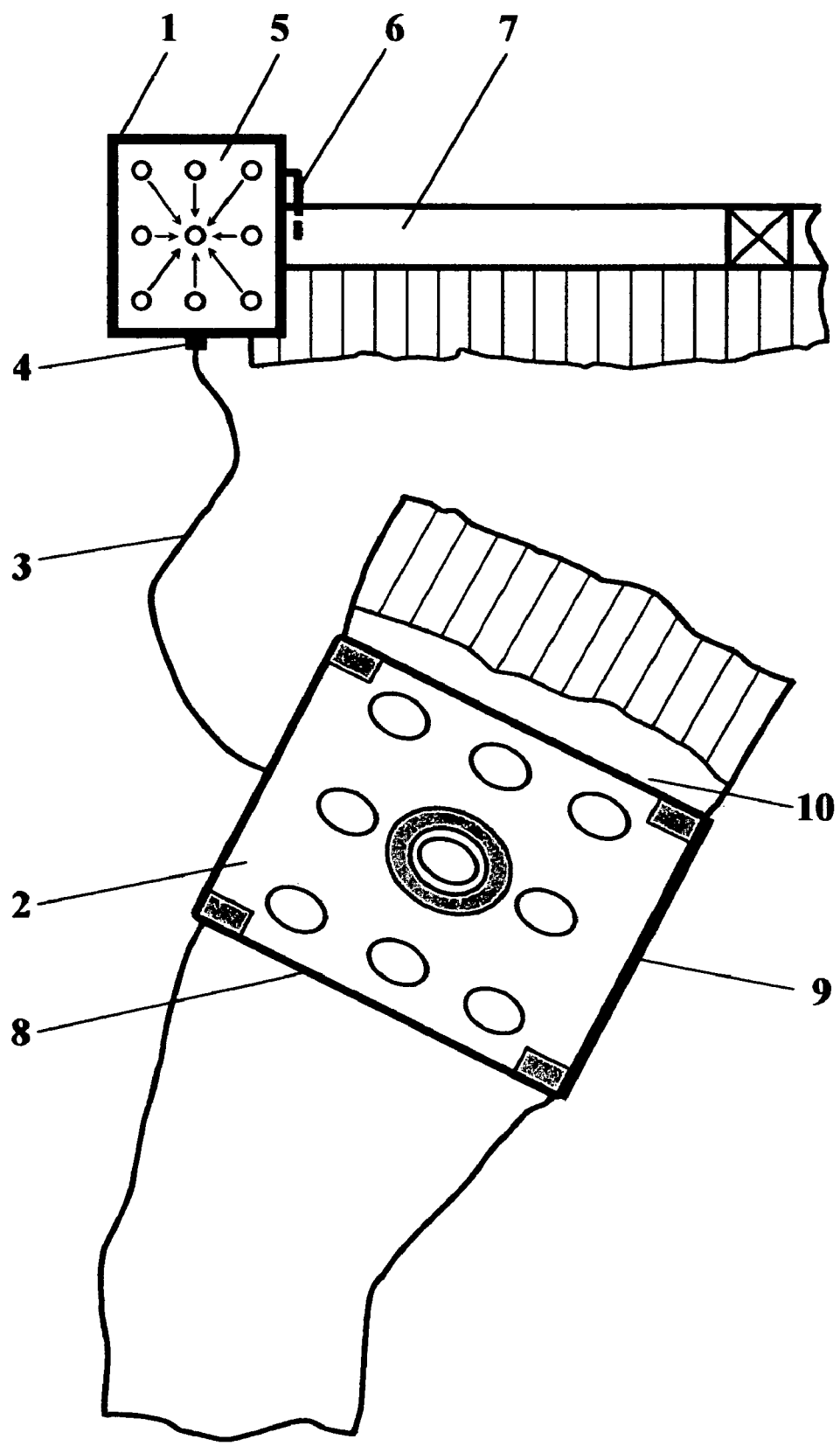
FIG. 1 is a view illustrating one of possible variants of an allocation of the functional components of dynamic binary temperature therapy system on a selected organism zone surface during a physiological procedure process, which realizes the new method of dynamic binary temperature therapy in accordance with the present invention.

One of the possible variants of an allocation of the functional components of dynamic binary temperature therapy system on a selected organism zone surface during a physiological procedure process is illustration in FIG. 1. Said dynamic system includes a microprocessor control block of automatic contrast thermocycling 1, which is electric connected with a nine-modules temperature applicator 2 by an electric multi-core flexible cable 3 through electric block connector 4. The microprocessor control block 1 has front touch screen panel 5, which provides the different possibilities for an input of given information and for an output of operating information about a working condition of the all functional system elements. A casing of said block 1 also has a resilient constructive element 6, which provides the possibility of fixing of said block on the different clothing elements (for example, on the trouser belt 7). The nine-modules temperature applicator 2 of so-called a "bandage" functional type includes a flexible contact material with low thermo conductivity 8 and an adhesive element 9 for bandage fixing of said applicator 2 on the selected application organism zone surface 10. In under consideration example said zone surface 10 is a postsurgical organism zone surface on the femoral portion of right foot, which includes the postsurgical seam, hematoma and tissue phlogosis.

Figure 2:
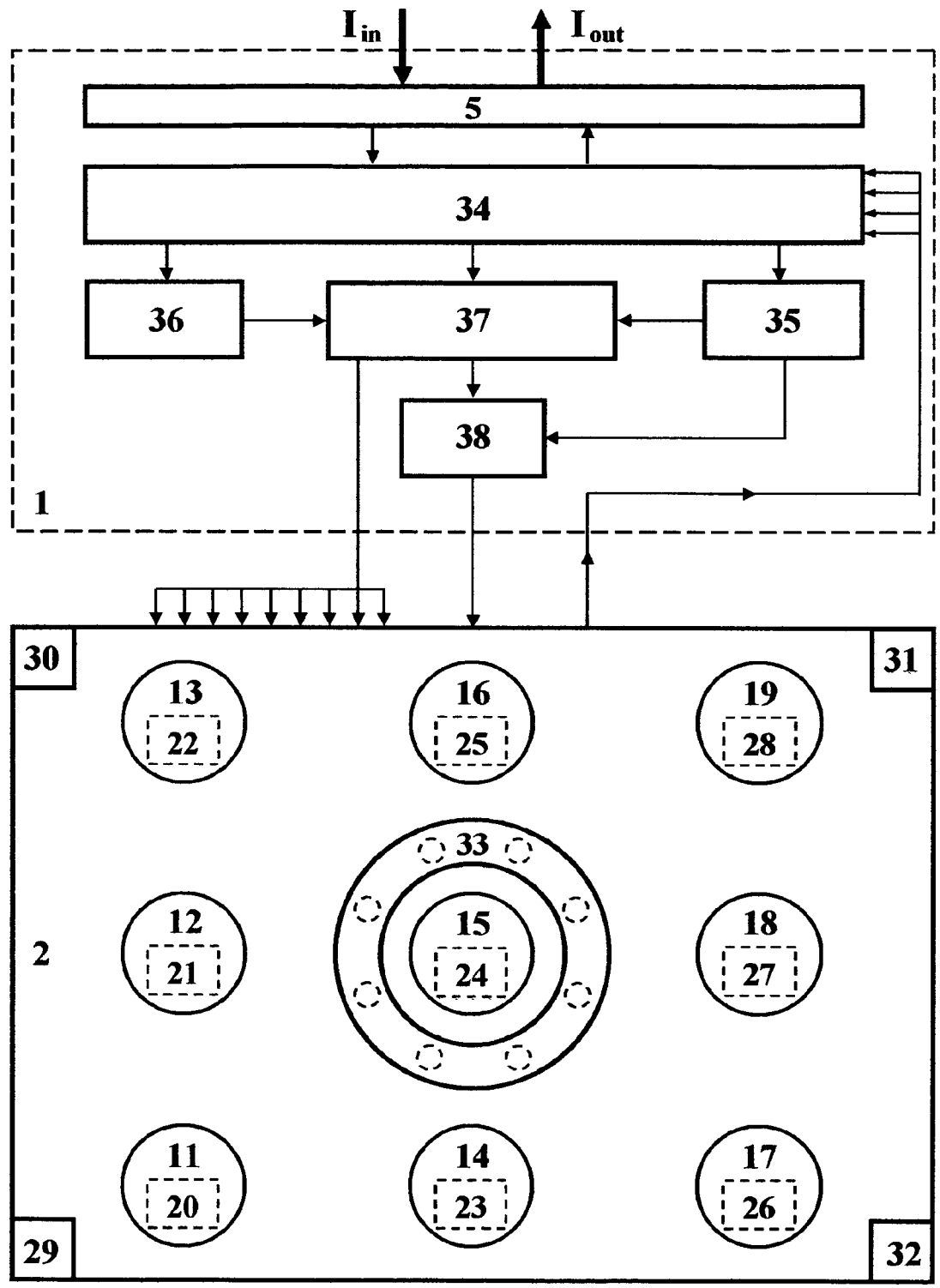
FIG. 2 is a view showing one of possible variants of a functional scheme of a dynamic binary temperature therapy system for providing a contrast differential-residual temperature action on a selected organism zone surface during a physiological procedure process, which realizes the new method of dynamic binary temperature therapy in accordance with the present invention.

The temperature applicator 2 also includes nine dynamic temperature modules 11-19, arranging per given longitudinal linear-parallel temperature action surface structure and contacting by contact surface of given oval form with a local portions of said organism zone surface, accordingly (FIG. 2). Each from the modules 11-19 includes a thermal element 20-28 accordingly, which is operating on the base of so-called Peltier Effect. The possible variant of a constructive schema of said temperature module is not shown in the drawings (are described in detail, for example in the above-mentioned our U.S. patent). Besides on the corners of said applicator 2 arranging four miniature temperature sensors 29-32 accordingly, which contact with said organism zone surface, and around said central temperature module 15 a multi-point circular electromagnetic dosing device 33 for delivery of medicamental preparation on a local portion of said application organism zone surface is located.

Said casing of microprocessor control block 1 comprises (besides said front touch screen panel 5) a microprocessor program unit 34, a phasing unit 35, a regime unit 36, a commutating unit 37 and a dosing unit 38. The above-mentioned block 1 including also and a block of energy supply comprises a source of direct current with a voltage stabilizer, which is not shown in the drawings. Accumulators, galvanic elements, photoelectric batteries, alternating current rectifiers connected to a network and other sources can be used as sources of direct current, which provide energy supply to the thermal elements 20-28 of said dynamic temperature modules 11-19, accordingly through said commutating unit 37, and also—to the above-mentioned panel 5 and all others units 34, 35, 36 and 38 of the microprocessor control block 1 (not shown in the drawings).

The above-mentioned front touch screen panel 5 of the control block 1 provides the different possibilities for an input of given information $I_{in}$ (as a modulation parametric input) and for an output of operating information $I_{out}$ about a working condition of the all functional system elements (FIG. 2). The touch screen panel 5 has information output and information input connected to the information input (or a modulation parametric input) and information output of the program unit 34 accordingly. At the same time, three information-controlling outputs of said program unit 34 are connected to the information-controlling inputs of said phasing unit 35, regime unit 36 and commutating unit 37 accordingly. Besides, four optimization parametric inputs of said program unit 34 are connected to parametric outputs of said four miniature temperature sensors 29-32 accordingly. The commutating unit 37 has also a regime input and a phasing input, which is connected to the controlling outputs of said regime unit 36 and phasing unit 35 accordingly. Herewith, one of the controlling outputs of commutating unit 37 is multi-channel electric connected to the thermal elements 20-28 of said dynamic temperature modules 11-19, accordingly. The second controlling output of commutating unit 37 is connected to the controlling input of said dosing unit 38, which has the controlling output is electric connected to said multi-point circular electromagnetic dosing device 33. Besides, the second controlling output of said phasing unit 35 is connected to the second controlling input of said dosing unit 38. At that all of the above-mentioned connections between the units 37, 34 and 38 of the microprocessor control block 1 and the functional elements 20-28 (or 11-19, accordingly), 29-32 and 33 of said temperature applicator 2 accordingly, are realized through said electric block connector 4 and electric multi-core flexible cable 3, accordingly (FIG. 2).

The above-described dynamic binary temperature therapy system for providing a contrast differential-residual temperature action on the selected organism zone surface during a physiological procedure process in accordance with the present invention operates in the following manner.

Prior to the commencement of said contrast differential-residual temperature action process, given information is inputted into the touch screen panel 5. Herewith, the user requesting from the program unit 34 to said touch screen the prior memorizing information about the initial modulation parameters of a planned modulating a value of said temperature action of each said dynamic temperature module: a frequency $f_m$ (to provide a modulation period $t_m$), a range $b_m$ (as a total of the absolute maximal phase amplitude of cooling temperature $T_{cm(max)}$ and heating temperature $T_{hm(max)}$ and a law $I_m$. Besides, the user requesting the prior memorizing information about the initial additional modulation parameters, including the characteristics of predetermined "drop-shaped" form phase law of the cooling phase (cooling phase law $I_{cm}$) and heating phase (heating phase law $I_{hm}$) with the predetermined values of phase duration $t_{cm}$ and $t_{hm}$, predetermined maximal temperature phase amplitudes $T_{cm(max)}$ and $T_{hm(max)}$, and also—the predetermined values of the above-mentioned time ratio $\alpha_{cm}=t_{Fcm}/t_{cm}$ and $\alpha_{hm}=t_{Fhm}/t_{hm}$ for the predetermined front times $t_{Fcm}$ and $t_{Fhm}$ into said predetermined phases, accordingly. The above-mentioned time ratios are selected from the range: more than 0 and less than 0.5.

The user can enter in the above-mentioned initial modulation parameters the any requisite corrections with take into consideration of speciality of the planned physiological procedure process and provide of the requisite contrast differential-residual temperature action on the selected organism zone surface. Herewith, he can use the touch screen possibilities for the visualization of the initial or/and planned diagrams of predetermined modulating with enters in the initial modulation parameters the requisite corrections. It has also the possibilities of additional enter in the modulation process, for example, a resting phase with predetermined resting duration (when a value of said temperature action is equal to null) after a termination of at least one from said cooling phase or/and a heating phase.

Besides, the user can selected one of the possible initial variants of a modulation phase regime, which forms the modulated gradients of differential-residual spatial wave temperature action in the selected application organism zone surface 10 by the forming dynamic temperature pairs of said nine-modules temperature applicator 2. Herewith said touch screen panel 5, said program unit 34 and said regime unit 36 are data connected. In the present example the memory of said regime unit 36 has five possible initial variants of modulation phase regime: so-called differential-residual spatial "longitudinal-diagonal wave", "cross-diagonal wave", "axial-nodal wave", "diagonal-nodal wave" and "central-nodal wave" temperature action. At said selecting the user can also observe a view illustrating the selected any said variant of modulation phase regime on the touch screen panel 5. The initial variant of modulation phase regime (for example, "longitudinal-diagonal wave") selecting with take into consideration of speciality of the planned physiological procedure process and provide of the requisite contrast differential-residual temperature action on the selected organism zone surface 10.

Herewith, the above-mentioned all selected initial modulation parametric and regime information memorize in the memory of said program unit 34, which provides all needful given information said units 35, 36 and 37. The regime and phasing information from said controlling outputs of said regime unit 36 and phasing unit 35 put in said commutating unit 37 through the regime and phasing inputs, accordingly. The commutating unit 37 provides given electric commutation of the electric connected thermal elements 20-28 of said dynamic temperature modules 11-19 accordingly, with take into consideration of the selected initial modulation phase regime (in this example—"longitudinal-diagonal wave") and given initial modulation phasing of the work of all said applicator modules. After the finishing of given electric commutation a value of electric current (from the above-mentioned block of energy supply), flowing through said all thermal elements 20-28, beginning permanently given modulation sign-alternating change with given modulation phasing of each thermal element, accordingly. Said given modulation and phase changes of said electric current are realized by the controllable multi-channel "power" electronic elements with phase-shift chains (for example, amplitude-phase controllable "power" controller) of said commutating unit 37 according, to given modulation and phase parameters, which are settled by said program unit 34 and said phasing unit 35 accordingly, connected to the information-controlling inputs of the unit 37 (FIG. 2).

At the same time, said unit 37 put in given value of electric current to the controlling input of said dosing unit 38 through the second controlling output, and said phasing unit 35 also put in given phasing information to the second controlling input of said dosing unit 38, which starting provide the impulse electric phasing control to said multi-point circular electromagnetic dosing device 33. Said given impulse electric phasing control of electric current is realized in said unit 38 by the controllable "power" electronic element (for example, controllable "power" trigger).

Figure 3:
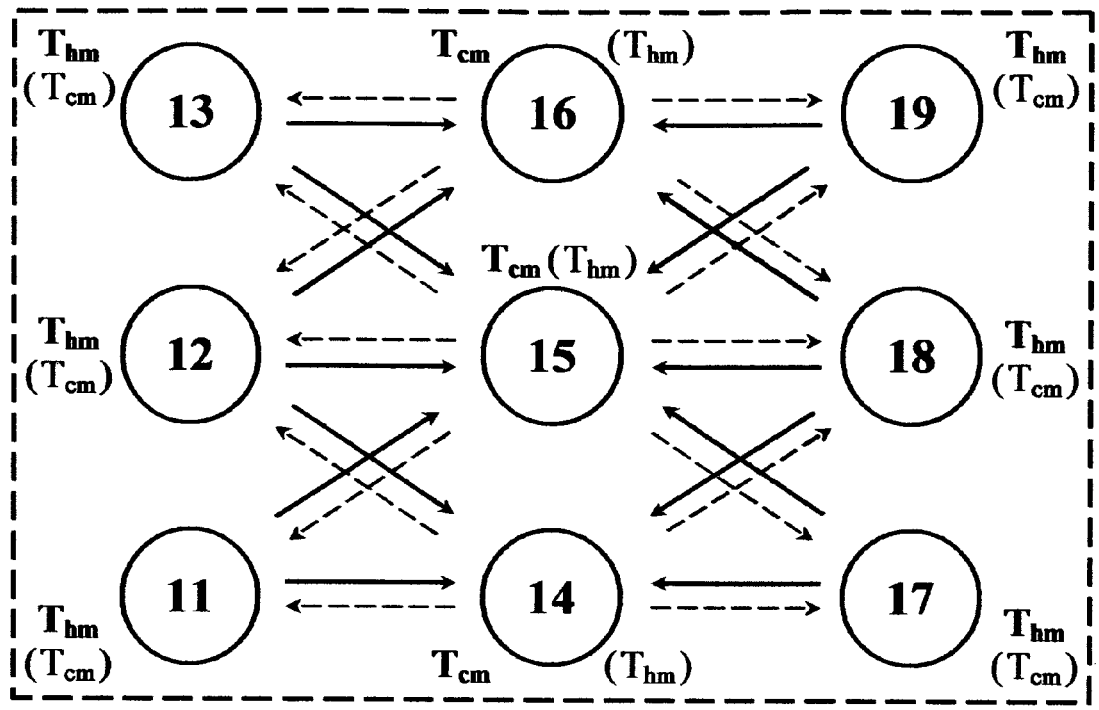
FIG. 3 is a view illustrating one of possible variants of a modulation phase regime, which forms the modulated gradients of so-called differential-residual spatial "longitudinal-diagonal wave" temperature action in an organism zone by the forming dynamic temperature pairs of nine-modules temperature applicator.

The above-mentioned given modulation phase regime, given parameters of modulating, given modulation phasing and also—arranging the dynamic temperature modules 11-19 per given longitudinal linear-parallel temperature action surface structure on the temperature applicator 2, provide the possible of planned realization of said selected initial variant of modulation phase regime of differential-residual spatial "longitudinal-diagonal wave" temperature action on the organism zone surface 10 by fourteen spatial forming dynamic temperature pairs of said nine temperature modules, accordingly. Each two side by side disposed said dynamic temperature modules, which working in differential-residual (binary) temperature modulation phase regime, form a modulated sign-alternating gradient of a differential-residual spatial temperature action in an organism zone surface portion, externally limited by a external borders of two a selected local zone surface portions is contacted with two said pair modules accordingly, for example the forming "longitudinal wave" module pairs: 11-14, 12-15, 13-16, 14-17, 15-18 and 16-19; or for example the forming "diagonal wave" module pairs: 11-15, 12-14, 12-16, 13-15, 14-18, 15-17, 15-19 and 16-18 (FIG. 3).

Figure 4:
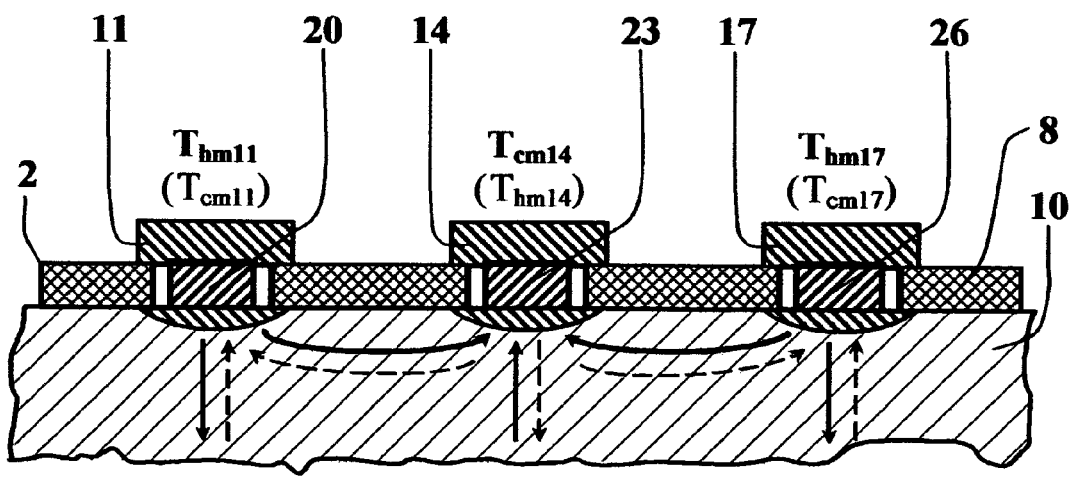
FIG. 4 is a view illustrating one of possible variants of a modulation phase regime, forming the modulated gradients of a differential-residual spatial temperature action in an organism zone portion by side by side disposed two a dynamic temperature pair with three the dynamic temperature modules of multi-modules temperature applicator.

In the FIG. 4 viewing an illustration of example of a form of the modulated gradients of a differential-residual spatial temperature action in an organism zone portion by two said dynamic temperature module pairs (11-14 and 14-17) with three the dynamic temperature modules 11, 14 and 17 of multi-modules temperature applicator 2. This example illustrating one the portion of under consideration multi-modules applicator structure, wherein said given temperature action surface structure is formed with use a serial disposition of related along formative line said dynamic temperature pairs with one joint said dynamic temperature module 14, which is collected for each two serial disposed said dynamic temperature pairs, each from which serial creates an antidirectional modulated sign-alternating gradient of a differential-residual spatial temperature action in a zone portion accordingly.

Herewith, given modulation change (with given modulation phasing) of a value of electric current, flowing through each from said thermal elements (20, 23 and 26) of said dynamic temperature modules (11, 14 and 17, accordingly) predetermine an analogical given modulation change (with given modulation phasing) of temperature action, which provides each from said modules on the contacted organism zone surface portion, accordingly. At that in illustrating time moment said temperature modules 11 and 17 provide the predetermined "drop-shaped" form heating phase law $I_{hm}$ (with heating phase temperature amplitudes $T_{hm11}$ and $T_{hm17}$, accordingly), and said temperature module 14 provides the predetermined "drop-shaped" form cooling phase law $I_{cm}$ with cooling phase temperature amplitude $T_{cm14}$, accordingly (see FIG. 4). This given temperature modulation moment predetermine provides the modulated temperature action gradients in said organism zone surface portion: as normal to the organism surfaces, which is contacted with said modules accordingly, so and the differential-residual—between said pair modules (see the solid lines, accordingly). In other illustrating time moment said temperature modules 11 and 17 will provide the predetermined "drop-shaped" form cooling phase law $I_{cm}$ (with cooling phase temperature amplitudes $T_{cm11}$ and $T_{cm17}$, accordingly), and said temperature module 14 will provides the predetermined "drop-shaped" form heating phase law $I_{hm}$ with heating phase temperature amplitude $T_{hm14}$, accordingly (see the marks in hooks, FIG. 4). This given temperature modulation moment predetermine provides the head analogous (to the above-mentioned temperature gradients) modulated temperature action gradients (see the dotted lines, accordingly).

Figure 5:
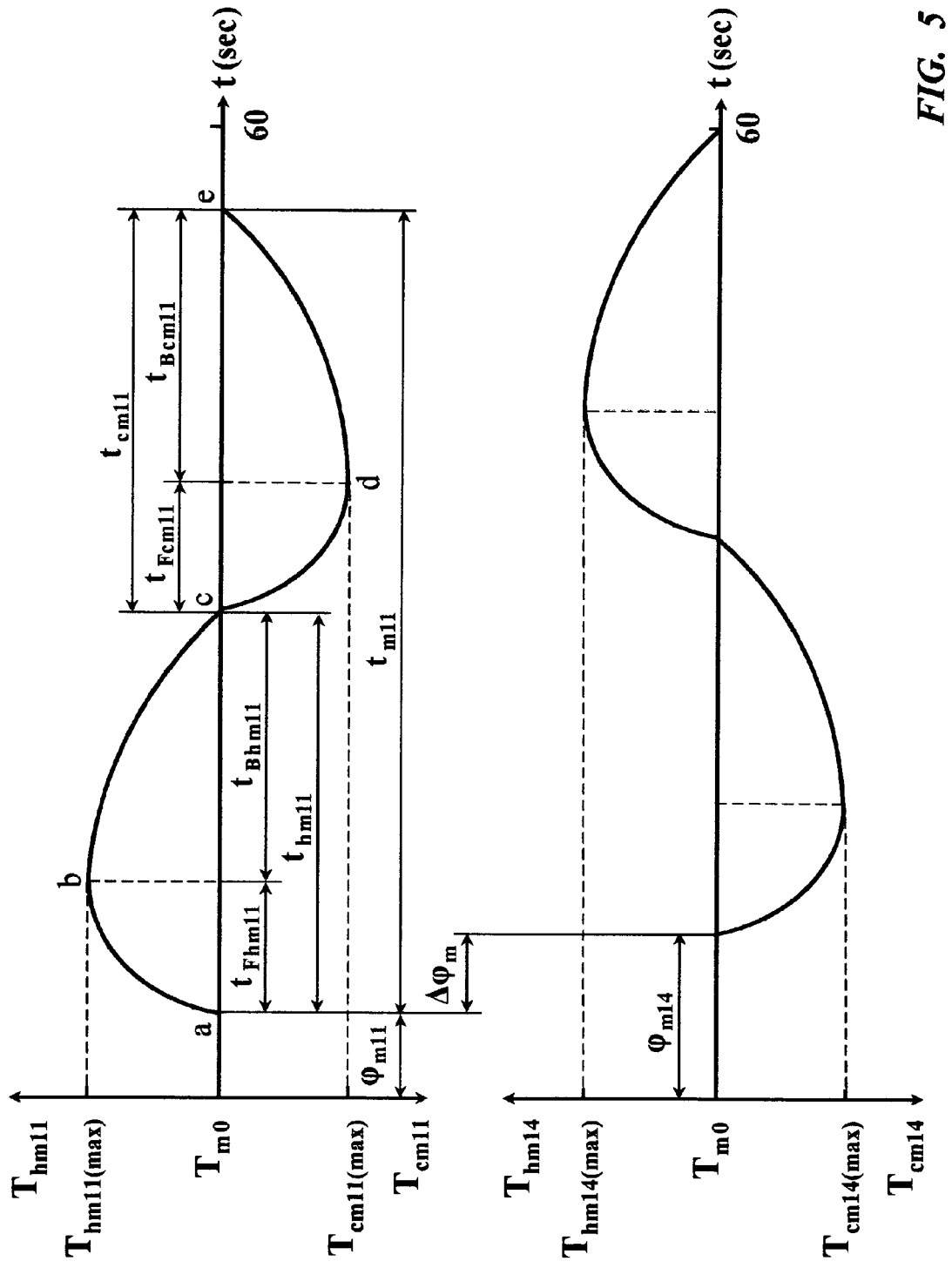
FIG. 5 is a view showing a diagram of an example of the general and additional independent predetermined modulating a value of temperature actions of first and second dynamic temperature modules of one a dynamic temperature pair simultaneously, including a cooling phase and a heating phase with predetermined "drop-shaped" form of said phase laws in each modulation period accordingly, and also—a phase shift, which optimization providing between a predetermined comparative phases of two said related modulating processes relatively.

In the FIG. 5 showing a diagram of an example of said predetermined modulating a value of temperature action of said dynamic temperature module 11, including a heating phase (with the duration $t_{hm11}$) and a cooling phase (with the duration $t_{cm11}$) with predetermined "drop-shaped" form of said phase laws (heating phase law $I_{hm11}$ and cooling phase law $I_{cm11}$) in each modulation period $t_{m11}$ accordingly, which providing:

increase of a value of said temperature action $T_{hm11}$ and $T_{cm11}$ from the initial null value $T_{m0}$ on said predetermined maximal phase amplitude $T_{hm11(max)}$ and $T_{cm11(max)}$ accordingly, during a predetermined front time ($t_{Fhm11}$ and $t_{Fcm11}$) of realizing a predetermined front short part of said phase law $I_{hm11(a-b)}$ (see the diagram part "a-b") and $I_{cm11(c-d)}$ (see the diagram part "c-d") accordingly, which is changed a form of a predetermined quarter ellipse curve such that a horizontal axis of said ellipse coincided with a horizontal axis of said "drop-shaped" form of said phase law $I_{hm11(a-b)}$ and $I_{cm11(c-d)}$; and decrease of a value of said temperature action $T_{hm11}$ and $T_{cm11}$ until said initial null value $T_{m0}$ during a predetermined back time ($t_{Bhm11}$ and $t_{Bcm11}$) of realizing a predetermined back extended part of said phase law $I_{hm11(b-c)}$ (see the diagram part "b-c") and $I_{cm11(d-e)}$ (see the diagram part "d-e") accordingly, which is changed a form of a predetermined degree function curve such that an until value of said degree function curve coincides with an ending value of said quarter ellipse curve $T_{hm11(max)}$ and $T_{cm11(max)}$ accordingly to provide a predetermined phase duration $t_{hm11}$ and $t_{cm11}$ accordingly, during each said modulation period $t_{m11}$; and also predetermined value of time ratio $\alpha_{hm11}=t_{Fhm11}/t_{hm11}$ and $\alpha_{cm11}=t_{Fcm11}/t_{cm11}$ accordingly, which is selected from said range: more than 0 and less than 0.5.

The above-mentioned time ratio ($\alpha_{hm11}$ or $\alpha_{cm11}$) is more one of an additional predetermined modulation parameter of said temperature modulating and can be changeable (optimizing automatically by said program unit 34 or by hand into the touch screen panel 5) in dependence on a change of a value of at least one a characteristic connected with the physiological processes of said organism for providing an optimizing maximal efficiency of said modulated differential-residual spatial temperature action during said physiological procedure process. Herewith, a predetermined value of time ratio of said heating and cooling phases in an each period of said temperature (cold-warm) action modulating can be the different or same, accordingly. Said changes of said value of time ratio can include:

changing a predetermined front time ($t_{Fhm11}$ or $t_{Fcm11}$) and providing a predetermined duration of heating (or cooling) phase ($t_{hm11}$ or $t_{cm11}$) simultaneously;

changing a predetermined duration of heating (or cooling) phase ($t_{hm11}$ or $t_{cm11}$) and providing a predetermined front time ($t_{Fhm11}$ or $t_{Fcm11}$) simultaneously;

changing a predetermined front time ($t_{Fhm11}$ or $t_{Fcm11}$) and a predetermined duration of heating (or cooling) phase ($t_{hm11}$ or $t_{cm11}$) simultaneously.

The above-mentioned so-called "drop-shaped form cooling/heating phase law" as general "drop-shaped" form phase law (for above-mentioned example of the cooling phase law $I_{cm11}$ in FIG. 4) is being described by two expressions:

$$I_{cm11(c-d)}=T_{m0}-T_{cm11(max)}\cdot[1-(1-t/t_{Fcm11})^2]^{1/2}$$

(for $t_{hm11} \leq t \leq t_{hm11}+t_{Fcm11}$); and $$I_{cm11(d-e)}=(T_{m0}-T_{cm11(max)})+T_{cm11(max)}\cdot(t-t_{Fcm11})^{\theta}/(t_{cm11}-t_{Fcm11})^{\theta}$$

(for $t_{hm11}+t_{Fcm11} \leq t \leq t_{m11}$);

where $\theta>1$ ( depends on $t_{Fcm11}$, $t_{cm11}$ and $T_{cm11(max)}$).

The author researches confirmed, that their proposed the optimal "drop-shaped form cooling/heating phase law" is most temperature-physiological efficient (in comparison with the another possible known forms of said phase law, for example: rectangular, sinusoidal, triangular, trapezoidal, elliptical, etc.). Besides, the optimal "drop-shaped" form phase law (takes into consideration its given naturally form) efficient joins all of the above-mentioned basic predetermined modulation parameters between them for their above-mentioned optimization. Besides, such "drop-shaped" form phase law of the dynamic change of a value of temperature action on said organism zone surface portion providing:

significant minimization of a possibility of dynamic temperature percussion action deformation of the tissue, capillary and vascular blood circulation structures in said application organism zone, which predetermine the above-mentioned "soft" ellipsoidal form of said front short part of said phase law (for example—$I_{cm11(c-d)}$) of input of a thermal energy by said dynamic temperature module; and "soft" dynamic take off said temperature action and recovery the initial temperature condition of the tissue, capillary and vascular blood circulation structures in said application organism zone, which predetermine the above-mentioned form of said back extended part of said phase law (for example—$I_{cm11(d-e)}$).

In the FIG. 5 also showing an optimization changeable phase shift $\Delta\phi_m$, which providing between a predetermined comparative phases of two said related modulating processes relatively: a predetermined comparative phase $\phi_{m11}$ of said general predetermined modulating a value of temperature action of said first dynamic temperature module 11 and a predetermined comparative phase $\phi_{m14}$ of the so-called additional independent second predetermined modulating a value of temperature action of second dynamic temperature module 14 of said dynamic temperature pair 11-14, simultaneously. Said optimization changing a value of said modulation parameter—said phase shift $\Delta\phi_m$ provides also in dependence on a change of a value of at least one a characteristic connected with the physiological processes of said organism for providing an optimizing maximal efficiency of said modulated differential-residual spatial temperature action, in the effective binary temperature gradient-wave manner, during said physiological procedure process. In this above-mentioned example said phase optimization of $\Delta\phi_m$ in said dynamic temperature pair 11-14 (as and in all other such forming temperature pairs in said modulation phase regime of differential-residual spatial "longitudinal-diagonal wave" temperature action) providing said phasing unit 35, which said controlling output is connected with said commutating unit 37 through the phasing input. Herewith, information for said phase optimization of $\Delta\phi_m$ said phasing unit 35 receives from said program unit 34, which computerizes the current measuring information from parametric outputs of four said miniature temperature sensors 29-32 accordingly, arranging on the applicator 2 and contacted with said organism zone surface 10 (see FIG. 2).

Said temperature sensors provide the current control of the temperature contour around said application organism zone surface 10 includes (in this example) the postsurgical seam, hematoma and tissue phlogosis and predetermines a temperature inhomogeneity per said controlled temperature contour by an inhomogeneity violation of physiological processes of blood circulation in the capillaries, arteries and veins of the selected application organism zone. Herewith, said information for said phase optimization of $\Delta\phi_m$, which receiving from said program unit 34, provide a change of said phase shifts at least one of said forming temperature pairs so that the realizing differential-residual spatial "longitudinal-diagonal wave" temperature action provides the maximal temperature equalization of said controlled temperature contour in said modulation phase regime. It is provided by the special program algorithm in said program unit 34, which realizes the correction as the spatial disposition of said pairs phase shifts, so and at least one of said modulation parameter of modulating the temperature action in the pairs dynamic temperature modules, accordingly.

Herewith, all "power" said optimization (modules/pairs) phasing or/and general modulation parametric changing realizes said commutating unit 37, which provides said all "power" sign-alternating changing the values of commutating electric currents, flowing through said each of all thermal elements 20-28, accordingly. The above-mentioned optimizing process predetermines the optimizing change the amplitudes of said modulated sign-alternating gradients of differential-residual (binary) spatial wave temperature action in said organism zone surface 10 (see FIG. 3). This process realizes the optimizing change of a spatial picture of said binary wave temperature action for providing the maximal temperature equalization of said controlled temperature contour in said differential-residual spatial "longitudinal-diagonal wave" modulation phase regime, that predetermines maximal efficiency of said modulated differential-residual spatial wave temperature action during said physiological procedure process.

Figure 6:
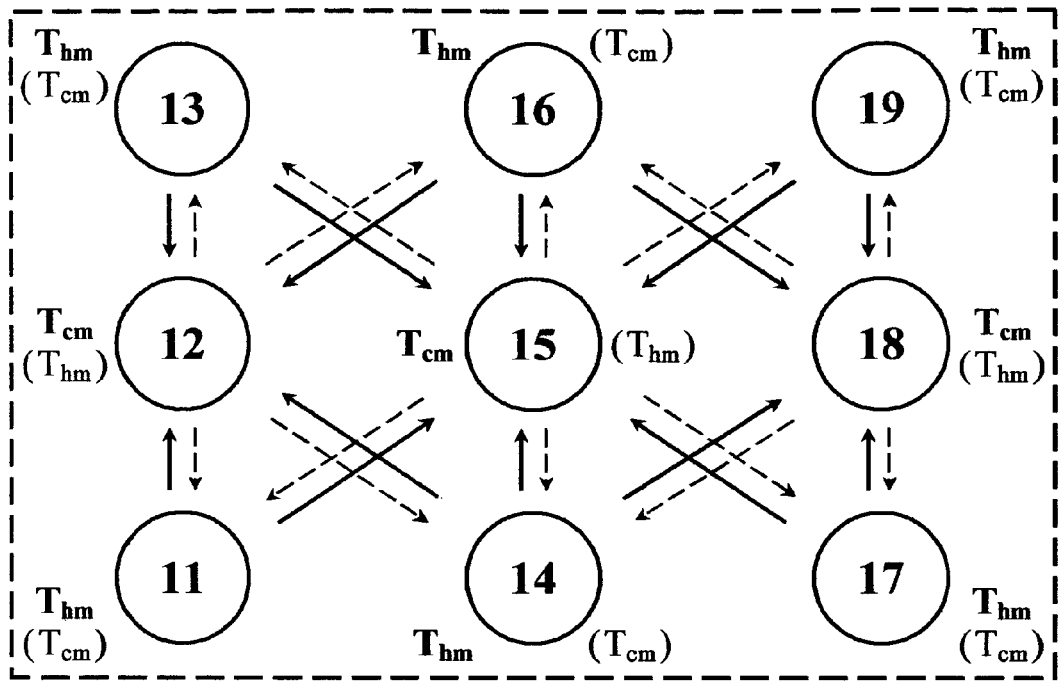
FIG. 6 is a view illustrating one of possible variants of a modulation phase regime, which forms the modulated gradients of so-called differential-residual spatial "cross-diagonal wave" temperature action in an organism zone by the forming dynamic temperature pairs of nine-modules temperature applicator.

The efficiency of the above-mentioned optimizing temperature action on said application organism zone surface 10 is in control predetermined time by said temperature sensors 29-32 accordingly. Provided that the special program algorithm in said program unit 34 establish circumstantially the insufficient efficiency of optimized temperature action, said program unit 34 forms information command to said regime input of regime unit 36 for the optimization change of next (for this example) possible variant of the modulation phase regime of co-called differential-residual spatial "cross-diagonal wave" temperature action (FIG. 6). Said regime will be realize per the above-mentioned scenario and provides new spatial picture of said binary wave temperature action with the optimizing changed modulated sign-alternating temperature gradients picture. For the new regime will be also realizing (in case needed) and other above-mentioned optimization correction as the spatial disposition of said pairs phase shifts, so and at least one of said modulation parameter of modulating the temperature action in the pairs dynamic temperature modules, accordingly.

Figure 7:
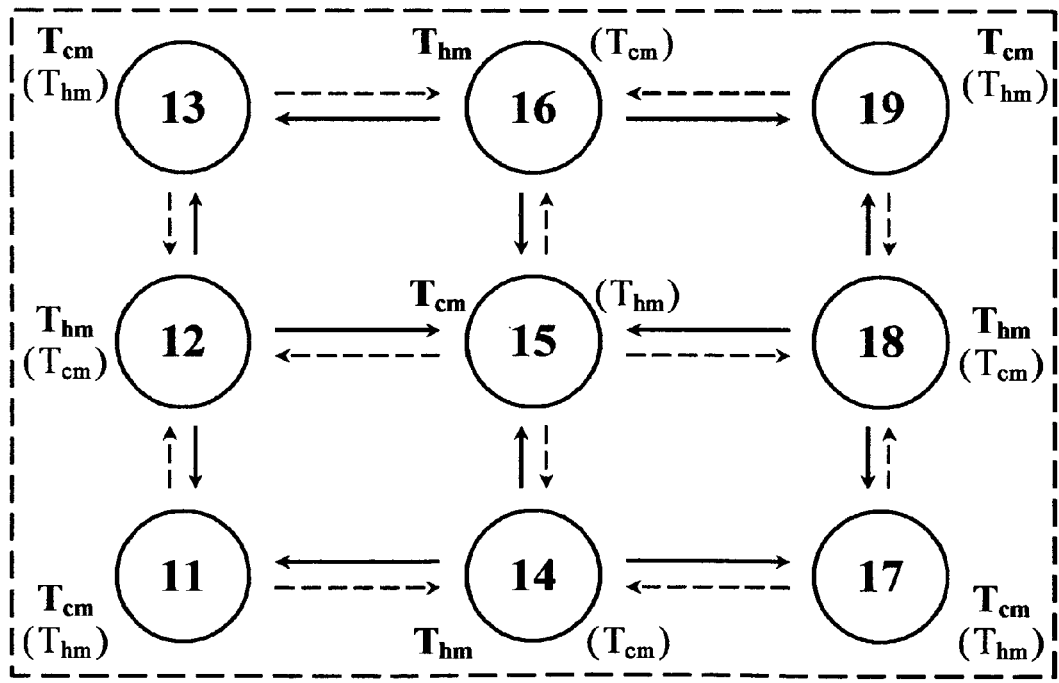
FIG. 7 is a view illustrating one of possible variants of a modulation phase regime, which forms the modulated gradients of so-called differential-residual spatial "axial-nodal wave" temperature action in an organism zone by the forming dynamic temperature pairs of nine-modules temperature applicator.
Figure 8:
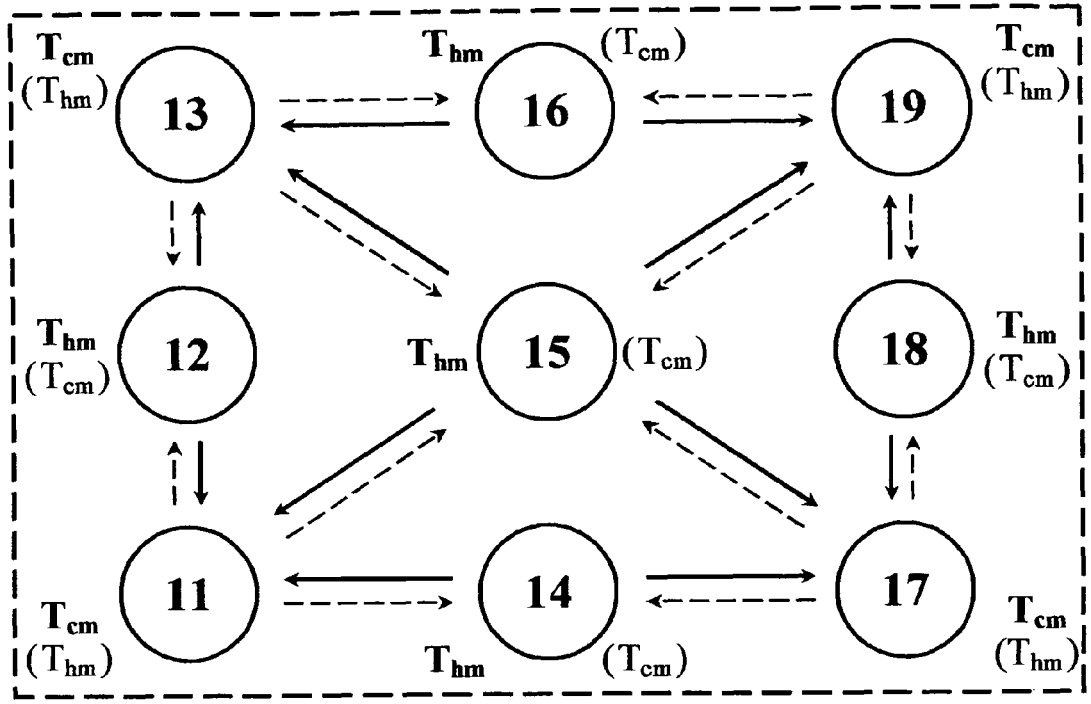
FIG. 8 is a view illustrating one of possible variants of a modulation phase regime, which forms the modulated gradients of so-called differential-residual spatial "diagonal-nodal wave" temperature action in an organism zone by the forming dynamic temperature pairs of nine-modules temperature applicator.
Figure 9:
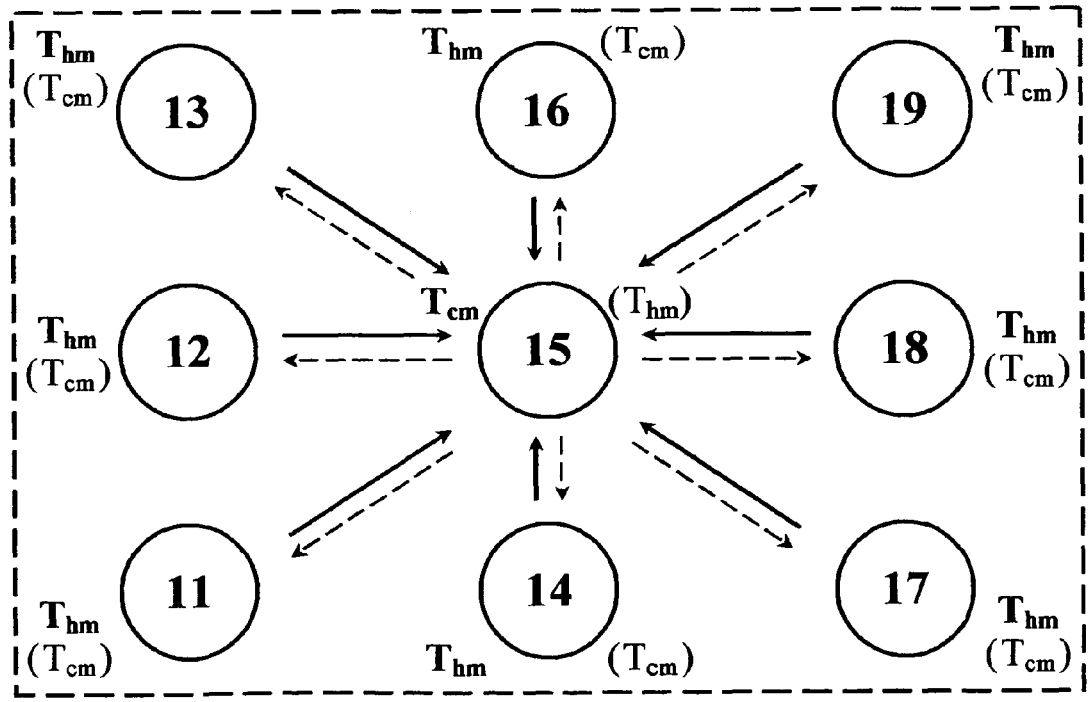
FIG. 9 is a view illustrating one of possible variants of a modulation phase regime, which forms the modulated gradients of so-called differential-residual spatial "central-nodal wave" temperature action in an organism zone by the forming dynamic temperature pairs of nine-modules temperature applicator.

The above-mentioned program unit 34 and regime unit 36 of microprocessor control block of automatic contrast thermocycling 1 (for this example) provide the optimizing change three more such different possible variant of the modulation phase regime of co-called:

the differential-residual spatial "axial-nodal wave" temperature action (see FIG. 7);

the differential-residual spatial "diagonal-nodal wave" temperature action (see FIG. 8);

the differential-residual spatial "central-nodal wave" temperature action (see FIG. 9).

Analyzing said efficiency of the above-mentioned optimizing temperature action on said application organism zone surface 10 with use said temperature sensors 29-32 accordingly, said program unit 34 periodically provides the optimizing change one from all five said the modulation phase regime by the special program algorithm for establish circumstantially the insufficient efficiency of optimized temperature action. Herewith, each said changeable regime will be also realizing per the above-mentioned scenario and provides new spatial picture of said binary wave temperature action with the optimizing changed and reallocation modulated sign-alternating temperature gradients and temperature nodal fields. At that said changed modulation phase regimes can also permanently observe on the touch screen panel 5 in color form, which is such the above-mentioned modulated sign-alternating temperature gradients pictures, illustrating in FIGS. 3, 6-9.

Said efficiency temperature action will be reflecting on the compensation of said temperature contour around said application organism zone surface 10 (includes, in this example, the postsurgical seam, hematoma and tissue phlogosis) by a progressive minimization (or radical elimination) the above-mentioned inhomogeneity violation of physiological processes of blood circulation in the capillaries, arteries and veins. Said efficiency providing the realization of physiological effective dynamic differential-residual contrast temperature (cold-warm) so-called "massage" and "wave smoothing" of blood circulation zone capillary/vascular system. Thus the proposed binary temperature (cold-warm) therapy actions is ordered on the treatment of said functional defections in said organism zone capillary and vascular structures, which significant influence on the vital physiological processes in zone tissues (so-called "binary temperature capillary/vascular therapy").

The above-mentioned optimization process full illustrates the proposed method of spatiotemporal temperature-physiological optimizing, included changing a value of at least one (or complex) said modulation parameter in dependence on a change of a value of at least one a characteristic connected with the physiological processes of said organism for providing an optimizing maximal efficiency of said modulated differential-residual spatial temperature action, in the effective binary temperature gradient-wave manner, during said physiological procedure process.

Figure 10:
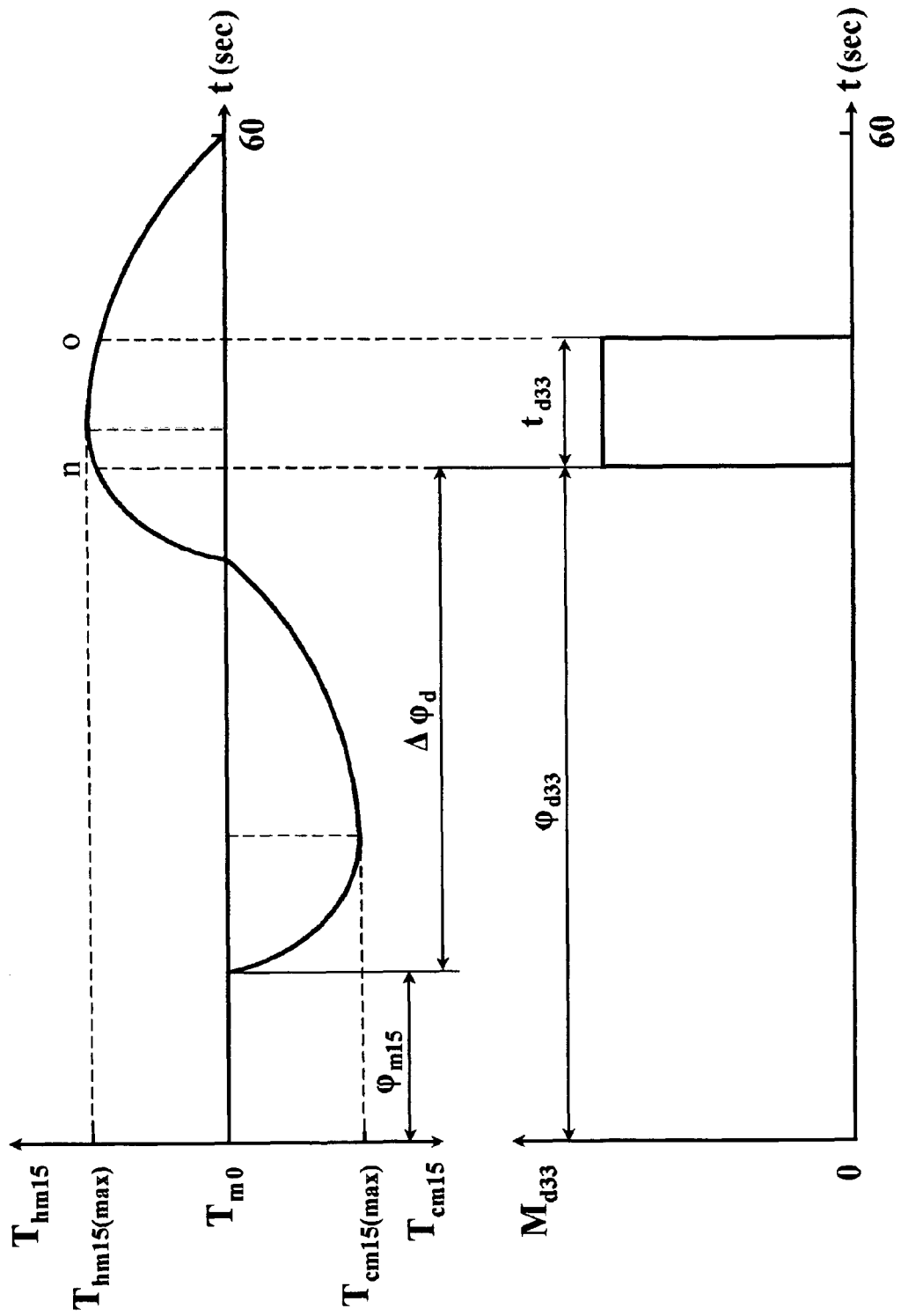
FIG. 10 is a view showing a diagram of an example of a predetermined modulating a value of temperature action of dynamic temperature module, including a cooling phase and a heating phase with predetermined "drop-shaped" form of said phase laws in each modulation period accordingly, and an independent predetermined periodic dosing process, which realizing simultaneously by a multi-point circular electromagnetic dosing device for delivery of medicamental preparation on a local portion of an application organism zone surface, and also—a phase shift, which optimization providing between a predetermined comparative phases of two said related processes relatively.

At the same time, the above-mentioned impulse phase-controllable process of dose delivery of medicamental preparation on said local portion of application organism zone surface 10 by the multi-point circular electromagnetic dosing device 33 (see FIG. 2) is the so-called independent predetermined periodic process, providing the predetermined independent periodic change of a value of additional other type action on said organism—a medicamental fluid medium action $M_{d33}$ with given duration $t_{d33}$. This medicamental fluid medium action providing around said central temperature module 15 and among others temperature modules to realize the periodically input of said medicamental fluid medium in said application organism zone surface 10 (includes, in this example, the postsurgical seam, hematoma and tissue phlogosis). To provide the maximal efficiency of the medicamental action on the physiological process in said organism zone each said periodic impulse dose delivery of medicamental medium must be realizes by the dosing device 33 in moment, when said local portion of organism zone surface 10 is the maximal warm up. Said effective moment corresponds the topping of heating phase of predetermined modulating a value of temperature action of dynamic temperature module 15 (see the diagram part "n-o" in FIG. 10).

To provide said moment said phasing unit 35 also put in given phasing information to the second controlling input of said dosing unit 38, which starting provide the impulse electric phasing control to said multi-point circular electromagnetic dosing device 33. Herewith providing given optimization phase shift $\Delta\phi_d$ between a predetermined comparative phase $\phi_{m15}$ of said predetermined modulating a value of temperature action of said dynamic temperature module 15 and a predetermined comparative phase $\phi_{d33}$ of said predetermined independent periodic change of a value of said additional other type medicamental fluid medium action $M_{d33}$ of said dosing device 33 (see FIG. 10). At that said providing of given optimization phase shift $\Delta\phi_d$ realizing by the above-mentioned optimizing change of any possible variant of the modulation phase regime. In this case said phase optimization provides the maximal effective of timing coordination of the impulse work of dosing device 33 and said dynamic temperature module 15, which realizes the additional function temperature "pseudo-pump" for said dosing medicamental fluid medium. Herewith significantly increasing the medicamental infiltration in porous structure of said application organism zone surface 10 and activating all said temperature-physiological therapeutical process.

The above-mentioned operation of one of possible variants of the dynamic binary temperature therapy system detail illustrates the all-general spatiotemporal temperature-physiological complex optimizing possibilities of the proposed new method of dynamic binary temperature therapy. Herewith, the different possible variants of the dynamic binary temperature therapy systems can be the specific development for different above-mentioned temperature-physiological therapeutical process. Such said program units can have the different special program algorithm to establish circumstantially of the insufficient efficiency of optimized wave temperature action, and also—can operating with the different banks of such the modulation phase regimes. Besides, said thermal elements of dynamic temperature modules can operating on the base of at least one know type of temperature action effect is selected from the group consisting of: electric-thermal, electro-magnetic, electro-chemical, electro-optical, laser and etc. Such thermal elements also will be electric connected with such block of automatic contrast thermocycling for providing an automatic optimizing modulation change of electric current, flowing through said thermal elements.

The above-mentioned such block of automatic contrast thermocycling can be as the portative (movable), so and the stationary or built-in in medical or another equipment. Herewith, the different possible variants of the dynamic binary temperature therapy systems can have the built n such multi-functional touch screen panel or can have the remote telescreen, and also—can have, for example, the possibilities of connection to the different computer or any another systems.

The possibilities of the above-mentioned use of optimizing control of different said characteristic connected with the physiological processes of application organism significantly expand the temperature-physiological therapeutical applications of the proposed new method. Thus, for example, for the dynamic binary temperature treatment of at least one known function physiological defection: headache, migraine, coronary insufficiency, neuropathical pain, functional spasm process, hemostasis process, haematomas process, swelling process, zone fracture, zone surgical seam, blood circulation violation in amputated zone, painful autosomatognosis, painful arthritis, locomotor apparatus violation, hair radical system violation, cosmetic violation or general brain-fag, can make free use of the optimization one- or/and multi-point control at least one said characteristic, which is connected with the physiological processes: blood pressure; vascular or capillary blood velocity; central, coupled, collapsing, identification, full or bounding pulse; local capillary pulsation; local or integral temperature; space organism zone temperature allocation; and etc.

Besides, the above-mentioned, without any limitation, proposed use of said additional other types of actions with said modulated differential-residual spatial temperature action on the application organism zone also significantly expand the temperature-physiological therapeutical applications of the proposed new method. Said possibilities of the significantly expand of new dynamic method applications are related with the above-mentioned proposed many different structure, form and type possible variants of the temperature applicators for such dynamic binary temperature therapy system.

At the first time proposed multi-vector wave spatiotemporal differential-residual contrast temperature (cold-warm) actions take into consideration the general role of brachiate capillary structures and wave processes between capillaries in said physiological processes of tissue blood circulation. The high physiological efficiency providing the realization of physiological effective dynamic differential-residual contrast temperature so-called "massage" and wave smoothing of blood circulation zone capillary/vascular systems (or so-called "temperature-dynamic physiological correction"). Thus the proposed binary temperature therapy actions is ordered on the treatment of said functional defections in said organism zone capillary and vascular structures, which significant influence on the vital physiological processes in zone tissues (so-called "binary temperature capillary/vascular therapy"). Herewith, the above-mentioned possibilities of the operational multi-point control of the temperature fields in the application organism zone surface will allow open wide possibilities to create the new revolutionary dynamic binary temperature therapy of known function physiological defection, without any limitation, for example: a headache; a migraine; a coronary insufficiency; a neuropathical pain; a functional spasm process; a hemostasis process; a haematomas process; a swelling process; a zone fracture; a zone surgical seam; a blood circulation violation in amputated zone; a painful autosomatognosis; and etc.

Realization of the developed revolutionary dynamic binary temperature therapy technologies will allow open wide possibilities to create the principally new class of mobile, household and professional such dynamic binary temperature therapy microprocessor systems. So, for example, the above-mentioned possibilities to create the principally new class of the different fabrics for different close-fitting clothes with a flexible network such multi-elements "thread-shaped" form binary temperature action applicators, which are constructively built-in into a fabric structure and continually contacted with organism zone surface, will allow open wide possibilities, for example, to increase the resisting functions and time of life of said organism. Besides, such dynamic binary temperature technologies will find the wide use for providing after-work relaxation of the personnel whose job requires significant mental efforts (computer users, financial workers, engineers and etc., as well as, for example, pilots or air traffic dispatchers), and also—in individual common applications with the purpose of relaxation and fatigue elimination (for instance, in a car or while watching TV, and etc.).

In fact, these therapy technologies may become the standard in the twenty first century and will mark a new era of the technical evolution in temperature therapy technologies, based on the new most spatiotemporal temperature-physiological effective modulation and optimization principles of the above-mentioned multi-point ultra- or low-frequency wave contrast temperature (cold-warm) actions. In addition, this also determines the possibility of obtaining a billion dollar economic effect connected with the solution of known humanitarian and social world problems.

It will be understood that each of the elements described above, or two or more together, may also find a useful application in other types of methods and devices differing from the types described above.

While the invention has been illustrated and described as embodied in the new method of dynamic binary temperature therapy, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. A method of dynamic spatiotemporal temperature-physiological optimization of a physiological process, in a dynamic temperature system with at least one block of automatic contrast thermocycling having a plurality of a dynamic temperature modules for providing a contrast temperature action on a zone of a surface of an organism, comprising the steps of selecting a zone of the surface of the organism for providing the contrast temperature action;
selecting on the selected zone a plurality of a local surface portions having a given form;
arranging to the plurality of the selected local surface portions a plurality of the dynamic temperature modules, having a given form of a contact surface corresponding to the form of the local surface portions, for providing at least one type of a surface structure of the contrast temperature action on the selected zone;
modulating a value of the contrast temperature action of at least one of the dynamic temperature modules having parameters for providing a modulating
with a comparative phase of the modulating providing a phase shift relative to a comparative phase of an independent predetermined periodic process for providing an additional action on the organism simultaneously with said modulating,
with a range of the modulating, providing a change of the value of the temperature action between a maximal value and a minimal value during a modulating period,
in accordance with a law of the modulating, providing a form of a change of the value of the temperature action during the modulating period,
with a frequency of the modulating which is selected to provide the modulating period including providing a cooling phase and a heating phase of the change of the value of the temperature action each with a phase law, a phase duration and a maximal phase amplitude, so that
said contrast temperature action of each two of the dynamic temperature modules disposed side by side form a dynamic temperature pair providing a modulated wave gradient of a differential-residual spatial temperature action in a portion of an organism zone externally limited by external borders of two of said selected local surface portions of the zone of the organism; and
changing a value of at least one parameter of the modulating in dependence on a change of a value of at least one characteristic connected with the physiological process of the organism for providing a maximal therapeutical efficiency of said action on the zone of the organism.

2. A method of spatiotemporal temperature-physiological optimization as defined in claim 1, further comprising including in said independent predetermined periodic process an independent predetermined periodic change of a value of at least one additional type action on said organism.

3. A method of spatiotemporal temperature-physiological optimization as defined in claim 2, further comprising using as said additional type action a mechanical action.

4. A method of spatiotemporal temperature-physiological optimization as defined in claim 2, further comprising using as said additional type action a vacuum action.

5. A method of spatiotemporal temperature-physiological optimization as defined in claim 2, further comprising using as said additional another type action type temperature action.

6. A method of spatiotemporal temperature-physiological optimization as defined in claim 2, further comprising using as said additional type action a light action.

7. A method of spatiotemporal temperature-physiological optimization as defined in claim 2, further comprising using as said additional type action a visual action.

8. A method of spatiotemporal temperature-physiological optimization as defined in claim 2, further comprising using as said additional type action a musical action.

9. A method of spatiotemporal temperature-physiological optimization as defined in claim 2, further comprising using as said additional type action an energy field action.

10. A method of spatiotemporal temperature-physiological optimization as defined in claim 2, further comprising using as said additional type action a fluid medium action.

11. A method of spatiotemporal temperature-physiological optimization as defined in claim 1, further comprising providing a multi-modules temperature applicator which cames said modules and forms at least one additional functional device.

12. A method of spatiotemporal temperature-physiological optimization as defined in claim 11, further comprising forming said at least one additional functional device as a dosing device for delivery of medicamental preparation on a local portion of said organism zone surface.

13. A method of spatiotemporal temperature-physiological optimization as defined in claim 11, further comprising forming said at least one additional functional device as a device of a different type of energy action on a local portion of said organism zone surface.

14. A method of spatiotemporal temperature-physiological optimization as defined in claim 11, further comprising forming said at least one additional functional device as an indicator of a dynamic change of temperature action on a local portion of said organism zone surface.

15. A method of spatiotemporal temperature-physiological optimization as defined in claim 11, further comprising forming said at least one additional functional device as a sensor for a control of said at least one characteristic connected with the physiological process of said organism.

16. A method of spatiotemporal temperature-physiological optimization as defined in claim 11, further comprising connecting said at least one additional functional device with a block of automatic contrast thermocycling.

17. A method of spatiotemporal temperature-physiological optimization as defined in claim 1, further comprising using as said phase law a predetermined "drop-shaped" form phase law providing increase of a value of said temperature action from an initial null value by said predetermined maximal phase amplitude during a predetermined front time of realizing a predetermined front short part of said phase law, and providing decrease of a value of said temperature action to said initial null value during a predetermined back time of realizing a predetermined back extended part of said phase law during a predetermined phase duration in each said modulation period.

18. A method of spatiotemporal temperature optimization as defined in claim 17, further comprising including in said predetermined "drop-shaped" form of said phase law providing a predetermined value of time ratio of said predetermined front time into said predetermined phase duration, which is selected from a range more than 0 and less than 0.5.

19. A method of spatiotemporal temperature-physiological optimization as defined in claim 18, further comprising providing said value of time ratio as an additional predetermined modulation parameter of said temperature action modulating, which changes in dependence on said change of a value of at least one a characteristic connected with said physiological process of said organism for providing a maximal therapeutical effective optimizing of said modulated temperature action, in a binary temperature gradient-wave manner, during said physiological process.

20. A method of spatiotemporal temperature-physiological optimization as defined in claim 17, further comprising changing said predetermined front short part of said "drop-shaped" form phase law in a form of a predetermined quarter ellipse curve such that a horizontal axis of said ellipse coincides with a horizontal axis of said phase law, and changing said predetermined back extended part of said phase law in a form of a predetermined degree function curve such that an initial value of said degree function curve coincides with an ending value of said quarter ellipse curve.

21. A method of spatiotemporal temperature-physiological optimization as defined in claim 1, further comprising providing a multi-modules temperature applicator which carries said modules and has at least one an element for fixing on said organism zone surface selected from the group consisting of a frontal-head, temporal-head or eye band, a head slam, a neck wrap, a face mask, a nose, auricular or general at least two-point clip, a shoulder, ancoenal, genicularor amputating cup, a bandage, a sticking-plaster, a bracelet, a spine stimulating tape, a glove, a sock, a hand or foot stimulating bath, and an internal stimulating applicator.

22. A method of spatiotemporal temperature-physiological optimization as defined in claim 21, further comprising forming said multi-modules temperature internal stimulating applicator as a bulk device with outside elastic form of multi-modules contract temperature action surface which is profile optimized by internal surface of said organism zone under an applicator mechanical action selected from the group consisting of an action of elastic deformation of said bulk device, an action of on elastic element on an interior surface of said bulk device, and an action of fluid medium pressured on interior surface of said bulk device.

23. A method of spatiotemporal temperature-physiological optimization as defined in claim 1, further comprising including in said independent predetermined periodic process an additional independent predetermined modulating of a value of said temperature action of said second dynamic temperature module of at least one said dynamic temperature pair, with said additional modulating comprising at least one of a cooling phase and a heating phase with a predetermined phase law, a phase duration and maximal phase amplitude.

24. A method of spatiotemporal temperature-physiological optimization as defined in claim 23, further comprising, after a termination of at least one of said cooling phase and said heating phase, providing an additional resting phase with a predetermined resting duration, when a value of said temperature action is equal to null.

25. A method of spatiotemporal temperature-physiological optimization as defined in claim 1, further comprising, after a termination of at least one of a cooling phase and a heating phase, providing an additional resting phase with a predetermined resting duration, when a value of said temperature action is equal to null.

26. A method of spatiotemporal temperature-physiological optimization as defined in claim 1, further comprising including in said temperature action modulating a modulation parametric input.

27. A method of spatiotemporal temperature-physiological optimization as defined in claim 1, further comprising including in said temperature action modulating an optimization parametric input.

28. A method of spatiotemporal temperature-physiological optimization as defined in claim 1, further comprising including in said independent predetermined periodic process providing a frequency, a range, a law and a comparative phase of predetermined periodic parametric change.

29. A method of spatiotemporal temperature-physiological optimization as defined in claim 1, further comprising including in said independent predetermined periodic process an additional independent predetermined modulating of a value of said temperature action of at least one dynamic temperature module of at least one said dynamic temperature pair, which is disposed in at least one temperature action surface structure of a multi-modules temperature applicator which cames said modules, with said additional modulating comprising at least one of a cooling phase and a heating phase with a predetermined phase law, a phase duration and maximal phase amplitude.

30. A method of spatiotemporal temperature-physiological optimization as defined in claim 1, further comprising including in said independent predetermined periodic process an additional independent predetermined modulating of a value of said temperature action of at least one dynamic temperature module of at least one said dynamic temperature pair, which is disposed in at least one temperature action surface structure of another multi-modules temperature applicator which cames other of said modules, providing a dynamic temperature action on another organism zone, with said additional modulating comprising at least one of a cooling phase and a heating phase with a predetermined phase law, a phase duration and maximal phase amplitude.

31. A method of spatiotemporal temperature-physiological optimization as defined in claim 1, further comprising selecting said characteristic connected with the physiological process of said organism from the group consisting of a blood pressure, a vascular or capillary blood velocity, a central, coupled, collapsing, identification, full or bounding pulse, a local capillary pulsation, a local or integral temperature, and a space organism zone temperature allocation.

32. A method of spatiotemporal temperature-physiological optimization as defined in claim 1, further comprising forming said given temperature action surface structure with a serial disposition of separate located along formative line at least two of said dynamic temperature pairs, each creating an unidirectional or antidirectional modulated gradient of a differential-residual spatial temperature action in a zone portion.

33. A method of spatiotemporal temperature-physiological optimization as defined in claim 1, further comprising forming said given temperature action surface structure with a serial disposition of located along formative line at least two of said dynamic temperature pairs with one common dynamic temperature module, each creating an antidirectional modulated gradient of a differential-residual spatial temperature action in a zone portion.

34. A method of spatiotemporal temperature-physiological optimization as defined in claim 1, further comprising selecting a given type of said temperature action surface structure of a disposition of said dynamic temperature modules from the group consisting of longitudinal linear, longitudinal nonlinear including sinusoidal, triangular, rectangular, trapezoidal or voluntary form, circular, coaxial-circular, a radially-circular, and a geometrical figure.

35. A method of spatiotemporal temperature-physiological optimization as defined in claim 1, further comprising disposing at least two of said temperature action surface structures together relative to each other on an application temperature action surface of a multi-modules temperature applicator which carries said modules in at least one variant selected from the group consisting of a series along formative line, a parallel with symmetrical or nonsymmetrical disposition of said dynamic temperature pairs, a series —parallel along formative line, a perpendicular, and another angle.

36. A method of spatiotemporal temperature-physiological optimization as defined in claim 1, further comprising providing in dynamic temperature modules a thermal element operating on Peltier Effect and electrically connected with a block of automatic contrast thermocycling which provides an automatic optimizing modulation change of electric current flowing through said thermal element.

37. A method of spatiotemporal temperature-physiological optimization as defined in claim 1, further comprising operating said thermal element of dynamic temperature modules with a temperature action effect selected from the group consisting of electric-thermal, electro-magnetic, electrochemical, electro-optical and laser, and electrically connecting said thermal element with a block of automatic contrast thermocycling which provides an automatic optimizing modulation change of electric current flowing through said thermal element.

38. A method of spatiotemporal temperature-physiological optimization as defined in claim 1, further comprising forming at least one of said dynamic temperature modules as an additional functional device.

39. A method of spatiotemporal temperature-physiological optimization as defined in claim 1, further comprising providing a block of automatic contrast thermocycling connected with an additional functional light indicator panel for a dynamic visualization of a spatiotemporal picture of a dynamic multi-point binary temperature action on said organism zone surface.

40. A method of spatiotemporal temperature-physiological optimization as defined in claim 1, further comprising providing a block of automatic contrast thermocycling connected with a multi-functional touch screen panel for an input of given modulation parametric information and for an output of operating information about a working condition of all functional system elements, and also —for a dynamic visualization of a spatiotemporal modulated sign-alternating temperature gradients pictures of a dynamic multi-point binary temperature action on said organism zone surface.

41. A method of spatiotemporal temperature-physiological optimization as defined in claim 1, further comprising providing a multi-modules temperature applicator which cames said modules and is connected with a functional structure of at least one another system with a working surface which is in contact with at least one organism zone surface, selected from the group consisting of a flexible fabric of close-fitting clothes, linen, glove, headdress, bed or shoes component, a surface of furniture component, a surface of car rudder, computer mouse or keyboard, glasses elements, headphones, wrist-watch, telephone, musical device, and medical equipment.

42. A method of spatiotemporal temperature-physiological optimization as defined in claim 1, further comprising arranging at least one of said dynamic temperature modules in a temperature action surface structure of a multi-modules temperature action applicator which is adjustable with a possibility of spatial disposition of at least one of said structure dynamic differential-residual temperature pairs.

43. A method of spatiotemporal temperature-physiological optimization as defined in claim 1, further comprising treating with the dynamic spatiotemporal temperature-physiological optimization of said physiological process to provide at least one known function physiological defection selected from the group consisting of a headache, a migraine, a coronary insufficiency, a neuropathical pain, a functional spasm process, a hemostasis process, a haematomas process, a swelling process, a zone fracture, a zone surgical seam, a blood circulation violation in amputated zone, a painful autosomatognosis, a painful arthritis, a locomotor apparatus violation, a hair radical system violation, a cosmetic violation, and a general brain-fag.

* * * * *